(12) United States Patent
Begemann

(10) Patent No.: US 11,708,580 B2
(45) Date of Patent: Jul. 25, 2023

(54) INCREASING PLANT GROWTH AND YIELD BY USING A DUF2996 DOMAIN-CONTAINING PROTEIN

(71) Applicant: Benson Hill, Inc., St. Louis, MO (US)

(72) Inventor: Matthew Begemann, St. Louis, MO (US)

(73) Assignee: Benson Hill, Inc., St. Louis, MO (US)

( * ) Notice: Subject to any disclaimer, the term of this patent is extended or adjusted under 35 U.S.C. 154(b) by 0 days.

(21) Appl. No.: 17/054,041

(22) PCT Filed: May 8, 2019

(86) PCT No.: PCT/IB2019/053796
§ 371 (c)(1),
(2) Date: Nov. 9, 2020

(87) PCT Pub. No.: WO2019/215648
PCT Pub. Date: Nov. 14, 2019

(65) Prior Publication Data
US 2021/0130840 A1 May 6, 2021

Related U.S. Application Data

(60) Provisional application No. 62/669,027, filed on May 9, 2018.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

U.S. PATENT DOCUMENTS 8,106,174 B2   1/2012   Kovalic et al.
8,344,211 B2 *  1/2013   Alexandrov ......... C07K 14/415
                                                          800/298

FOREIGN PATENT DOCUMENTS

WO   WO 2013/128448 A1   9/2013
WO   WO-2017070458 A2 *  4/2017   ......... C12N 15/8261

OTHER PUBLICATIONS

Kaur et al. "Differentially expressed seed aging responsive heat shock protein OsHSP18.2 implicates in seed vigor, longevity and improves germination and seedling establishment under abiotic stress". Frontiers in plant science. 6(713): 1-13 (Year: 2015).*
Heyno et al. "A dual role for plant quinone reductases in host-fungus interaction". Physiologia Plantarum. 149(3):340-353 (Year: 2013).*
Fan, X., et al., The NdhV subunit is required to stabilize the chloroplast NADH dehydrogenase-like complex in *Arabidopsis*, *The Plant Journal*, 2015, vol. 82(2), pp. 221-231.

* cited by examiner

*Primary Examiner* — Matthew R Keogh
*Assistant Examiner* — David R Byrnes
(74) *Attorney, Agent, or Firm* — Womble Bond Dickinson (US) LLP

(57) ABSTRACT

Compositions and methods for improving plant growth are provided herein. Polynucleotides encoding DUF2996 domain-containing protein s, polypeptides encompassing DUF2996 domain-containing protein s, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

10 Claims, No Drawings
Specification includes a Sequence Listing.

INCREASING PLANT GROWTH AND YIELD BY USING A DUF2996 DOMAIN-CONTAINING PROTEIN

CROSS-REFERENCE TO RELATED APPLICATIONS

This application is a national stage filing under 35 U.S.C. 371 of PCT/IB2019/053796 filed May 8, 2019, which International Application was published by the International Bureau in English on Nov. 14, 2019, and application claims priority from U.S. Provisional Patent Application No. 62/669,027, filed May 9, 2018, which applications are hereby incorporated in their entirety by reference in this application.

FIELD OF THE INVENTION

The invention is drawn to compositions and methods for increasing plant growth and yield through expression of a gene encoding a DUF2996-containing protein in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to precisely modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance, photosynthetic carbon assimilation rates, and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in the metabolic pathways that contribute to plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth resulting in higher crop yield. Such methods include increasing the expression of at least one gene encoding a DUF2996 domain-containing protein in a plant of interest. The invention also encompasses constructs comprising a promoter that drives expression in a plant cell operably linked to a coding sequence encoding a DUF2996 domain-containing protein. Compositions further comprise plants, plant seeds, plant organs, plant cells, and other plant parts that have increased expression of a sequence encoding a DUF2996 domain-containing protein. The invention includes methods that can be utilized to increase expression of a gene encoding a DUF2996 domain-containing protein in a plant. Such gene encoding a DUF2996 domain-containing protein may be a native sequence or alternatively, may be a sequence that is heterologous to the plant of interest.

Embodiments of the invention include:

1. A method for increasing crop yield comprising transforming a plant with at least one coding sequence encoding a DUF2996 domain-containing protein.
2. The method of embodiment 1, wherein said coding sequence encoding a DUF2996 domain-containing protein comprises SEQ ID NO:1, or encodes a protein selected from the group consisting of SEQ ID NOs:2 and 7-67.
3. The method of embodiment 1, wherein said coding sequence encoding a DUF2996 domain-containing protein encodes a protein with at least 80%, 90%, 95%, 96%, 97%, 98%, or 99% sequence identity to a sequence selected from the group consisting of SEQ ID NOs:2 and 7-67, and that has [crop yield-increasing] function.
4. The method of embodiment 1, wherein said coding sequence encoding a DUF2996 domain-containing protein encodes a protein with at least 80%, 85%, 90%, 95%, 96%, 97%, 98%, or 99% sequence positives relative to a sequence selected from the group consisting of SEQ ID NOs:2 and 7-67, and that has [crop yield-increasing] function.
5. A plant having stably incorporated into its genome a promoter that drives expression in a plant operably linked to a coding sequence encoding a DUF2996 domain-containing protein, wherein said promoter is heterologous to said coding sequence encoding a DUF2996 domain-containing protein.
6. The plant of embodiment 5, wherein said coding sequence encoding a DUF2996 domain-containing protein comprises SEQ ID NO:1, or encodes a protein selected from the group consisting of SEQ ID NOs:2 and 7-67.

7. The plant of embodiment 5, wherein said coding sequence encoding a DUF2996 domain-containing protein encodes a protein with at least 80%, 85%, 90%, 95%, 96%, 97%, 98%, or 99% sequence identity to a sequence selected from the group consisting of SEQ ID NOs:2 and 7-67, and that has [crop yield-increasing] function.
8. The plant of embodiment 5, wherein said coding sequence encoding a DUF2996 domain-containing protein encodes a protein with at least 80%, 85%, 90%, 95%, 96%, 97%, 98%, or 99% sequence positives relative to a sequence selected from the group consisting of SEQ ID NOs:2 and 7-67, and that has [crop yield-increasing] function.
9. Transformed seed of any one of the plants of embodiments 5-8.
10. The plant of any one of embodiments 5-8 wherein said plant is a monocot.
11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena,* or *Hordeum*.
12. The plant of any one of embodiments 5-8 wherein said plant is a dicot.
13. The plant of embodiment 12 wherein said plant is from the genus *Glycine, Brassica, Medicago, Helianthus, Carthamus, Nicotiana, Solanum, Gossypium, Ipomoea, Manihot, Coffea, Citrus, Theobroma, Lactuca, Chenopodium, Cichorium, Camellia, Persea, Ficus, Psidium, Mangifera, Olea, Carica, Anacardium, Macadamia, Prunus, Beta, Populus,* or *Eucalyptus*.
14. The plant of any one of embodiments 5-8 wherein said plant exhibits increased growth relative to a control plant.
15. The plant of any one of embodiments 5-8 wherein said plant exhibits increased biomass yield relative to a control plant.
16. The plant of any one of embodiments 5-8 wherein said plant exhibits increased seed yield relative to a control plant.
17. The method of any one of embodiments 1-4, wherein said coding sequence encoding a DUF2996 domain-containing protein is expressed from a bundle sheath cell-preferred promoter.
18. The method of embodiment 17, wherein said bundle sheath cell-preferred promoter comprises SEQ ID NO:3.
19. The plant of any one of embodiments 5-8, wherein said promoter that drives expression in a plant is a bundle sheath cell-preferred promoter.
20. The plant of embodiment 19, wherein said bundle sheath cell-preferred promoter comprises SEQ ID NO:3.
21. The plant of embodiment 5 having stably incorporated into its genome a second promoter that drives expression in a plant operably linked to a second protein-encoding sequence, wherein said second promoter is heterologous to said second protein-encoding sequence.
22. A DNA construct comprising, in operable linkage,
   a. A promoter that is functional in a plant cell and,
   b. A nucleic acid sequence encoding a DUF2996 domain-containing protein.
23. The DNA construct of embodiment 22, wherein said nucleic acid sequence encoding a DUF2996 domain-containing protein comprises SEQ ID NO:1, or encodes a protein selected from the group consisting of SEQ ID NOs:2 and 7-67.
24. The DNA construct of embodiment 22 or 23, wherein said nucleic acid sequence encoding a DUF2996 domain-containing protein encodes a protein with at least 80%, 85%, 90%, 95%, 96%, 97%, 98%, or 99% sequence identity to a sequence selected from the group of SEQ ID NOs:2 and 7-67, and that has [crop yield-increasing] function.
25. The DNA construct of embodiment 22 or 23, wherein said nucleic acid sequence encoding a DUF2996 domain-containing protein encodes a protein with at least 80%, 85%, 90%, 95%, 96%, 97%, 98%, or 99% sequence positives relative to a sequence selected from the group consisting of SEQ ID NOs:2 and 7-67, and that has [crop yield-increasing] function.
26. The DNA construct of embodiment 22 or 23, wherein said promoter that is functional in a plant cell comprises SEQ ID NO:3.
27. The DNA construct of any one of embodiments 22-26, wherein said promoter is heterologous to said nucleic acid sequence encoding a DUF2996 domain-containing protein.
28. A method for increasing crop yield comprising modulating the expression of at least one coding sequence encoding a DUF2996 domain-containing protein in a plant.
29. The method of embodiment 28 wherein said modulating the expression comprises increasing the expression of at least one coding sequence encoding a DUF2996 domain-containing protein in a plant.
30. The method of embodiment 29, wherein said increasing the expression comprises increasing the activity of a native sequence encoding a DUF2996 domain-containing protein in said plant or increasing activity of a native coding sequence encoding a DUF2996 domain-containing protein in said plant.
31. The plant of any one of embodiments 5-8, wherein said promoter that drives expression in a plant is active in leaf tissue.
32. The DNA construct of any one of embodiments 22-27, wherein said promoter that is functional in a plant cell is active in leaf tissue.

DETAILED DESCRIPTION OF THE INVENTION

Compositions and methods for increasing crop biomass and yield are provided. The methods include increasing the expression of at least one gene encoding a DUF2996 domain-containing protein in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found below-ground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding a DUF2996 domain-containing protein. In a preferred embodiment, the expression of a DUF2996 domain-containing protein-encoding gene is upregulated relative to expression levels of genes encoding DUF2996 domain-containing proteins in a control plant, resulting in increased harvestable biomass in plants with increased expression of genes encoding DUF2996 domain-containing proteins relative to control plants. Any methods for increasing the activity or expression of a coding sequence encoding a DUF2996 domain-containing protein in a plant are encompassed by the present invention.

The compositions of the invention include constructs comprising the coding sequences set forth in SEQ ID NO:1 or encoding a protein selected from the group of SEQ ID NOs:2 and 7-67 or variants thereof, operably linked to a promoter that is functional in a plant cell. By "promoter" is intended to mean a regulatory region of DNA that is capable of driving expression of a sequence in a plant or plant cell. It is recognized that having identified the DUF2996 domain-containing protein sequences disclosed herein, it is within the state of the art to isolate and identify additional DUF2996 domain-containing protein sequences and nucleotide sequences encoding DUF2996 domain-containing protein sequences, for instance through BLAST searches, PCR assays, and the like.

The coding sequences of the present invention, when assembled within a DNA construct such that a promoter is operably linked to the coding sequence of interest, enable expression and accumulation of DUF2996 domain-containing protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the DUF2996 domain-containing protein s of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the DUF2996 domain-containing protein-encoding nucleotide sequence. While the DUF2996 domain-containing protein-encoding nucleotide sequence and the promoter sequence are heterologous to each other, either the DUF2996 domain-containing protein-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain [crop yield-increasing] function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as catalyzing the conversion of quinone and NAD(P)H to quinol and NAD(P)$^+$. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

Classes of Amino Acids

| Amino Acid Class | Example Amino Acids |
| --- | --- |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding DUF2996 domain-containing protein s, i.e. upregulating expression. Likewise, in some instances, plant growth and yield may be increased by decreasing the expression levels of one or more genes encoding DUF2996 domain-containing protein s, i.e. downregulating expression. Thus, the invention encompasses the upregulation or downregulation of one or more genes encoding DUF2996 domain-containing protein s. Further, the methods include the upregulation of at least one gene encoding a DUF2996 domain-containing protein and the downregulation of at least one gene encoding a second DUF2996 domain-containing protein in a plant of interest. By modulating the concentration and/or activity of at least one of the genes encoding a DUF2996 domain-containing protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding DUF2996 domain-containing protein s of the present invention can be controlled by the use of one or more promoters that are functional in a plant cell. The expression level of the DUF2996 domain-containing protein-encoding gene of interest may be measured directly, for example, by assaying for the level of the gene encoding a DUF2996 domain-containing protein transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. DUF2996 domain-containing protein function can be assessed by, for example, [expressing a DUF2996 domain-containing protein in a plant of interest and assessing biomass and/or seed yield of the transformed plants relative to the biomass and/or seed yield of control plants].

A "subject plant or plant cell" is one in which genetic alteration, such as transformation, has been effected as to a DUF2996 domain-containing protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of a DUF2996 domain-containing protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of a DUF2996 domain-containing protein-encoding gene of interest, antisense constructions, complementary to at least a portion of the messenger RNA (mRNA) for the sequences of a gene of interest, particularly a gene encoding a DUF2996 domain-containing protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding DUF2996 domain-containing protein s can be identified and used in the methods of the invention. The variant sequences will retain the biological activity of a DUF2996 domain-containing protein (i.e., catalyzing the conversion of quinone and NAD(P)H to quinol and NAD(P)$^+$). The present invention shows that, unexpectedly, certain novel expression strategies for DUF2996 domain-containing protein overexpression can lead to increased biomass and seed yield.

The expression cassette will include in the 5'-3' direction of transcription, a transcriptional and translational initiation region, a polynucleotide encoding a DUF2996 domain-containing protein of the present invention, and a transcriptional and translational termination region (i.e., termination region) functional in plants.

A number of promoters may be used in the practice of the invention. The polynucleotides encoding a DUF2996 domain-containing protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding DUF2996 domain-containing protein s of the invention may be expressed from tissue-preferred promoters. Tissue-preferred promoters include Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant* 4(3):495-505. Leaf-preferred promoters are also known in the art. See, for example, Yamamoto et al. (1997) *Plant* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Developmentally-regulated promoters may be desirable for the expression of a polynucleotide encoding a DUF2996 domain-containing protein. Such promoters may show a peak in expression at a particular developmental stage. Such promoters have been described in the art, e.g., U.S. 62/029, 068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding a DUF2996 domain-containing protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding a DUF2996 domain-containing protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding DUF2996 domain-containing protein s of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lecl transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc.*

*Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), quinoa (*Chenopodium quinoa*), chicory (*Cichorium intybus*), lettuce (*Lactuca sativa*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding a DUF2996 domain-containing protein of the present invention is used to transform a plant cell or cells. The transformed plant cell or cells are regenerated to produce transformed plants. These plants transformed with a construct comprising a functional promoter driving expression of a DUF2996 domain-containing protein-encoding polynucleotide of the invention demonstrated increased plant yield, i.e., increased above-ground biomass and/or increased harvestable biomass and/or increased seed yield.

Now that it has been demonstrated that upregulation of genes encoding a DUF2996 domain-containing protein increases plant yield, other methods for increasing expression of an endogenous sequence encoding a DUF2996 domain-containing protein in a plant of interest can be used. The expression of a gene encoding a DUF2996 domain-containing protein present in a plant's genome can be altered by inserting a transcriptional enhancer upstream of the gene encoding a DUF2996 domain-containing protein present in the plant's genome. This strategy will allow the gene encoding a DUF2996 domain-containing protein's expression to retain its normal developmental profile, while showing elevated transcript levels. This strategy will occur through the insertion of an enhancer element upstream of a gene encoding a DUF2996 domain-containing protein of interest using a meganuclease designed against the genomic sequence of interest. Alternatively, a Cas9 endonuclease coupled with a guide RNA (gRNA) designed against the genomic sequence of interest, or a Cpf1 endonuclease coupled with a gRNA designed against the genomic sequence of interest, or a Csm1 endonuclease coupled with a gRNA designed against the genomic sequence of interest is used to effect the insertion of an enhancer element upstream of a gene encoding a DUF2996 domain-containing protein of interest. Alternatively, a deactivated endonuclease (e.g., a deactivated Cas9, Cpf1, or Csm1 endonuclease) fused to a transcriptional enhancer element is targeted to a genomic location near the transcription start site for a gene encoding a DUF2996 domain-containing protein of interest, thereby modulating the expression of said gene encoding a DUF2996 domain-containing protein of interest (Piatek et al. (2015) *Plant Biotechnol J* 13:578-589).

Modulation of the expression of a DUF2996 domain-containing protein-encoding gene may be achieved through the use of precise genome-editing technologies to modulate the expression of the endogenous sequence. In this manner, a nucleic acid sequence will be inserted proximal to a native plant sequence encoding the DUF2996 domain-containing protein through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163:759-771, U.S. Provisional Patent Application 62/295,325); *N. gregoryi* Argonaute-mediated DNA insertion (Gao et al. (2016) *Nat Biotechnol* doi:10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression, decreased expression, and/or altered expression profile of a gene encoding a DUF2996 domain-containing protein.

Enhancers include any molecule capable of enhancing gene expression when inserted into the genome of a plant. Thus, an enhancer can be inserted in a region of the genome upstream or downstream of a sequence encoding a DUF2996 domain-containing protein of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding a DUF2996 domain-containing protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of gene encoding a DUF2996 domain-containing protein expression may also be achieved through the modification of DNA in a way that does not alter the sequence of the DNA. Such changes could include modifying the chromatin content or structure of the gene encoding a DUF2996 domain-containing protein of interest and/or of the DNA surrounding the gene encoding a DUF2996 domain-containing protein. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the gene encoding a DUF2996 domain-containing protein of interest and/or of the DNA surrounding the gene encoding a DUF2996 domain-containing protein of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the gene encoding a DUF2996 domain-containing protein of interest may be applied in order to achieve the desired result of an altered gene encoding a DUF2996 domain-containing protein expression profile.

Alteration of gene encoding a DUF2996 domain-containing protein expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding a DUF2996 domain-containing protein may be achieved by inserting a transposable element upstream of the gene encoding a DUF2996 domain-containing protein of interest, causing the expression of said gene to be altered.

Alteration of gene encoding a DUF2996 domain-containing protein expression may also be achieved through expression of a transcription factor or transcription factors that regulate the expression of the gene encoding a DUF2996 domain-containing protein of interest. It is well understood that alteration of transcription factor expression can in turn alter the expression of the target gene(s) of said transcription factor (Hiratsu et al. (2003) *Plant J* 34:733-739). Alteration of gene encoding a DUF2996 domain-containing protein expression may be achieved by altering the expression of transcription factor(s) that are known to interact with a gene encoding a DUF2996 domain-containing protein of interest.

Alteration of gene encoding a DUF2996 domain-containing protein expression may also be achieved through the insertion of a promoter upstream of the open reading frame encoding a native DUF2996 domain-containing protein in the plant species of interest. This will occur through the insertion of a promoter of interest upstream of a DUF2996 domain-containing protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-cpf1, CRISPR-Csm1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of DUF2996 Domain-Containing Protein Plant Transformation Vectors An open reading frame encoding a maize DUF2996 domain-containing protein was synthesized. This open reading frame comprised SEQ ID NO:1, encoding the protein sequence of SEQ ID NO:2. Appropriate restriction sites were included at the 5' and 3' ends of the coding sequences to allow this DNA to be cloned into plant transformation vectors that contained genetic elements suitable for controlling gene expression. In each plant transformation construct, the open reading frame encoding a DUF2996 domain-containing protein was located downstream of a plant promoter and 5' untranslated region (5'UTR) and upstream of a 3'UTR. Table 2 summarizes the plant transformation constructs that were built containing a DUF2996 domain-containing protein-encoding open reading frame.

TABLE 2

DUF2996 domain-containing protein
plant transformation constructs

| Construct | Promoter | ORF | 3'UTR |
|---|---|---|---|
| 131447 | GLDC (SEQ ID NO: 3) | GRMZM2G128072 (SEQ ID NO: 1, encoding SEQ ID NO: 2) | ZmRbcS (SEQ ID NO: 6) |
| 131448 | ZmRbcS (SEQ ID NO: 4) | GRMZM2G128072 (SEQ ID NO: 1, encoding SEQ ID NO: 2) | ZmRbcS (SEQ ID NO: 6) |
| 132683 | GLDC (SEQ ID NO: 3) | GRMZM2G128072 (SEQ ID NO: 1, encoding SEQ ID NO: 2) | ZmRbcS (SEQ ID NO: 6) |
| 132714 | ZmRbcS7A (SEQ ID NO: 5) | GRMZM2G128072 (SEQ ID NO: 1, encoding SEQ ID NO: 2) | ZmRbcS (SEQ ID NO: 6) |

In addition to the gene cassettes described in Table 2, each plant transformation construct listed in Table 2 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Table 2 contained the desired sequences, they were transformed into *A. tumefaciens* cells for plant transformation. Alternatively, the constructs listed in Table 2 are used for plant transformation via biolistic particle bombardment.

Example 2—Transformation of Setaria viridis

*A. tumefaciens* cells harboring DUF2996 domain-containing protein plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 3 summarizes the transformation constructs used to transform *S. viridis*, along with the number of PCR-verified transgenic plants that resulted from transformation with each construct.

TABLE 3

Summary of S. viridis transformation with DUF2996 domain-
containing protein plant transformation vectors

| Construct | # Events |
|---|---|
| 131447 | 32 |
| 131448 | 29 |

Example 3—Transformation of Maize (Zea mays)

*A. tumefaciens* cells harboring DUF2996 domain-containing protein plant transformation vectors are used to transform maize (*Zea mays* cv. B104) cells suitable for regeneration on tissue culture medium. Following transformation of the maize cells with the relevant plant transformation vectors and regeneration of maize plants, PCR analyses are performed to confirm the presence of the gene(s) of interest in the maize genome.

Example 4—Transformation of Rice (Oryza sativa)

*A. tumefaciens* cells harboring DUF2996 domain-containing protein plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic S. viridis

Following the transformation and regeneration of *S. viridis* plants transformed with a DUF2996 domain-containing protein plant transformation vector, the T0-generation plants were cultivated to maturity to produce T1-generation seeds. T1-generation *S. viridis* plants harboring the gene encoding a DUF2996 domain-containing protein cassette of interest were grown in a greenhouse setting to assess the effects of gene encoding a DUF2996 domain-containing protein expression on plant growth and terminal aboveground biomass and seed yield. A randomized block design was used with a wild-type *S. viridis* border row to eliminate edge effects from the analysis. Null segregant plants were grown alongside the transgenic *S. viridis* plants in identical environmental conditions. T1 plants were allowed to self-pollinate and T2-generation seeds were harvested from those self-pollinations. Table 4 summarizes the results of the biomass and seed yield determinations made from experiments with T1-generation (experiments S82 and S98) and T2-generation (experiment U23) *S. viridis* plants harboring a gene encoding a DUF2996 domain-containing protein cassette as a result of transformation. This table indicates the construct used for transformation, as described in Table 2, followed by the T0 event number from which the T1 seed was harvested.

TABLE 4

Summary of S. viridis greenhouse observations
with T1-generation plants

| Experiment | Event | DW (g) | Seed Yield (g) | DW Change | Seed Change |
|---|---|---|---|---|---|
| S98 | 131447-12 | 3.37 ± 0.25 | 0.71 ± 0.06 | −11.3% | −32.4% |
| | 131447-14 | 4.23 ± 0.18 | 1.09 ± 0.05 | 11.3% | 3.8% |
| | 131447-15 | 3.85 ± 0.21 | 0.90 ± 0.06 | 1.3% | −14.3% |
| | 131447-22 | 4.96 ± 0.16 | 1.43 ± 0.08 | 30.5% | 36.2% |
| | 131447-24 | 4.64 ± 0.16 | 1.22 ± 0.04 | 22.1% | 16.2% |
| | 131447-3 | 3.93 ± 0.18 | 0.93 ± 0.06 | 3.4% | −11.4% |
| | 131447-null | 3.80 ± 0.19 | 1.05 ± 0.07 | n/a | n/a |
| U23 | 131447-12 | 5.11 ± 0.22 | 1.08 ± 0.06 | −2.5% | 0.9% |
| | 131447-14 | 5.31 ± 0.14 | 1.03 ± 0.04 | 1.3% | −3.7% |
| | 131447-15 | 5.14 ± 0.23 | 1.03 ± 0.08 | −1.9% | −3.7% |
| | 131447-22 | 5.51 ± 0.12 | 1.15 ± 0.04 | 5.2% | 7.5% |
| | 131447-24 | 5.18 ± 0.15 | 1.12 ± 0.04 | −1.1% | 4.7% |
| | 131447-3 | 5.38 ± 0.12 | 1.16 ± 0.05 | 2.7% | 8.4% |
| | 131447-null | 5.24 ± 0.10 | 1.07 ± 0.04 | n/a | n/a |
| S82 | 131448-13 | 3.40 ± 0.17 | 0.65 ± 0.06 | 1.0% | 5.9% |
| | 131448-15 | 3.32 ± 0.30 | 0.60 ± 0.08 | −1.3% | −2.1% |
| | 131448-20 | 3.19 ± 0.13 | 0.65 ± 0.04 | −5.1% | 6.4% |
| | 131448-21 | 2.56 ± 0.16 | 0.44 ± 0.05 | −23.8% | −27.8% |
| | 131448-25 | 2.69 ± 0.21 | 0.51 ± 0.05 | −20.1% | −16.4% |
| | 131448-28 | 2.86 ± 0.31 | 0.46 ± 0.09 | −15.1% | −25.7% |
| | 131448-null | 3.37 ± 0.24 | 0.61 ± 0.05 | n/a | n/a |

In Table 4, the dry weight of the above-ground biomass is indicated in the DW column in grams. Similarly, the dry weight of the harvested seeds is indicated in grams in the Seed Yield column. The DW Change and Seed Change columns indicate the percent change in above-ground biomass and seed yield, respectively, relative to the null segregants from the appropriate construct. As this table shows, event 131447-22 produced both biomass and seed yield increases in both the T1 and T2 generations; events 131447-14 and 131447-3 produced biomass increases in both the T1 and T2 generations, and 131447-24 produced seed yield increases in both the T1 and T2 generations. Most of the 131448 events resulted in decreased biomass and seed yield relative to null segregant controls in experiment S82.

Example 6—Characterization of Transgenic Maize

T0-generation maize plants transformed with the DUF2996 domain-containing protein plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the gene encoding a DUF2996 domain-containing protein cassette and any other relevant gene cassettes (e.g., a selectable marker gene cassette) that were included in the DUF2996 domain-containing protein plant transformation vector. Following the maturation of the maize plants, the seed is harvested. Seeds from the plants containing the gene encoding a DUF2996 domain-containing protein cassette are pooled, as are seeds from the null segregant plants lacking the gene encoding a DUF2996 domain-containing protein cassette. The seeds are weighed, and seed yields are calculated for the plants containing the gene encoding a DUF2996 domain-containing protein cassette as well as for the null segregant plants lacking the gene encoding a DUF2996 domain-containing protein cassette. Appropriate statistical analyses are performed to determine whether plants containing a DUF2996 domain-containing protein gene cassette produce higher yields than those plants that lack a gene encoding a DUF2996 domain-containing protein cassette.

Alternatively, T0-generation maize plants transformed with the DUF2996 domain-containing protein plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the gene encoding a DUF2996 domain-containing protein cassette are pooled, as are seeds from the null segregant plants lacking the gene encoding a DUF2996 domain-containing protein cassette. The seeds are weighed, and seed yields are calculated for the plants containing the gene encoding a DUF2996 domain-containing protein cassette as well as for the null segregant plants lacking the gene encoding a DUF2996 domain-containing protein cassette. Appropriate statistical analyses are performed to determine whether plants containing a gene encoding a DUF2996 domain-containing protein cassette produce higher yields than those plants that lack a gene encoding a DUF2996 domain-containing protein cassette.

Example 7—Characterization of Transgenic Rice

T0-generation rice plants transformed with the DUF2996 domain-containing protein plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing a gene encoding a DUF2996 domain-containing protein cassette produce higher yields than those plants that lack a gene encoding a DUF2996 domain-containing protein cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing a gene encoding a DUF2996 domain-containing protein cassette produce higher yields than those plants that lack a gene encoding a DUF2996 domain-containing protein cassette.

I claim:

1. A method for increasing crop yield comprising transforming a plant with at least one coding sequence encoding a DUF2996 domain-containing protein wherein said coding sequence encoding a DUF2996 domain-containing protein shares at least 95% identity with SEQ ID NO:1, or encodes a protein having an amino acid sequence that shares at least 95% identity with the amino acid sequence of SEQ ID NO: 2, and wherein expression of said coding sequence increases yield in said plant;
   wherein said DUF2996 domain-containing protein possesses the biological activity of catalyzing the conversion of quinone and NAD(P)H to quinol and NAD(P)$^+$;
   wherein said coding sequence encoding a DUF2996 domain-containing protein is expressed from a bundle sheath cell-preferred promoter comprising SEQ ID NO: 3.

2. A plant having stably incorporated into its genome a promoter that drives expression in a plant operably linked to a coding sequence encoding a DUF2996 domain-containing protein wherein said coding sequence encoding a DUF2996 domain-containing protein shares at least 95% identity with SEQ ID NO:1, or encodes a protein having an amino acid sequence that shares at least 95% identity with the amino acid sequence of SEQ ID NO:2 wherein said promoter is heterologous to said coding sequence encoding a DUF2996 domain-containing protein;
   wherein said DUF2996 domain-containing protein possesses the biological activity of catalyzing the conversion of quinone and NAD(P)H to quinol and NAD(P)$^+$;
   wherein said promoter that drives expression in a plant is a bundle sheath cell-preferred promoter comprising SEQ ID NO:3.

3. The plant of claim 2 wherein said plant is a monocot.

4. The plant of claim 2 wherein said plant is a dicot.

5. A DNA construct comprising, in operable linkage,
   a. a promoter that is functional in a plant cell and comprises SEQ ID NO: 3, and
   b. a nucleic acid sequence encoding a DUF2996 domain-containing protein, wherein said nucleic acid sequence encoding a DUF2996 domain-containing protein comprises a sequence that shares at least 95% identity with SEQ ID NO:1, or encodes a protein having an amino acid sequence that shares at least 95% identity with the amino acid sequence of SEQ ID NO:2;
   wherein said DUF2996 domain-containing protein possesses the biological activity of catalyzing the conversion of quinone and NAD(P)H to quinol and NAD(P)$^+$;
   wherein said promoter is heterologous to said nucleic acid sequence encoding the DUF2996 domain-containing protein.

6. The method of claim 1 wherein said coding sequence encoding a DUF2996 domain-containing protein comprises SEQ ID NO:1, or encodes a protein having the amino acid sequence of SEQ ID NO:2.

7. The plant of claim 2 wherein said coding sequence encoding a DUF2996 domain-containing protein comprises SEQ ID NO:1, or encodes a protein having the amino acid sequence of SEQ ID NO:2.

8. The DNA construct of claim 5 wherein said nucleic acid sequence encoding a DUF2996 domain-containing protein comprises SEQ ID NO:1, or encodes a protein having the amino acid sequence of SEQ ID NO:2.

9. The method of claim 1, wherein the crop yield increase in said plant comprises increase in above-ground biomass, and/or increase in harvestable biomass, and/or increase in seed yield.

10. The plant of claim 2, wherein the crop yield increase in said plant comprises increase in above-ground biomass, and/or increase in harvestable biomass, and/or increase in seed yield.

* * * * *

SEQUENCE LISTING

```
<160> NUMBER OF SEQ ID NOS: 67

<210> SEQ ID NO 1
<211> LENGTH: 648
<212> TYPE: DNA
<213> ORGANISM: Zea mays
<220> FEATURE:
```

```
<221> NAME/KEY: misc_feature
<222> LOCATION: (1)..(648)
<223> OTHER INFORMATION: DUF2996 domain-containing gene

<400> SEQUENCE: 1
atggtcatgg cgcctcagcc ttcgcgcgct ctgagtccga ggctgagccg cgccccggc        60 gccggccacg cgtcgtgcag gtgctcggca gcgctcgcgc cgctcttcgg gaagcgcccg       120
gcgcccctcg tggtgtcgtt cccgcgcgcc ggcagcggcg gcgccgtcgc ctcctgctcg       180
gccgtgccgg tgcaggagtc gtccacctcc accgctgtta gcaagaagaa ggacggtgcc       240
aataaggagg ccacagcggc caagccgaag aaggccgcgg cgctgccgct gccggagatg       300
atgcaggagg agatcatccc gccgctgaag gccgccttgg aggcggagga ggacgtgtcc       360
caggtccagc tcgccttcga aaacaacacg ctagagggat ccttcataaa ggacgacgtc       420
ccttattgtt tctgggcctt ctttccaaaa ggagacctca caggacccaa gggcttcgcg       480
ctatcgtcct acagcaacga ggtgagcacc atcgagccgt tcctgatcga cgagaagagg       540
gtaacggcca agtacgtggt gttctgggtt tacaagagcg tggctgggca aggcatcctt       600
ccggtctgga aggaagagga ggggaggat catcaggacg ccaagtag                    648

<210> SEQ ID NO 2
<211> LENGTH: 215
<212> TYPE: PRT
<213> ORGANISM: Zea mays
<220> FEATURE:
<221> NAME/KEY: MISC_FEATURE
<222> LOCATION: (1)..(215)
<223> OTHER INFORMATION: DUF2996 domain-containing protein

<400> SEQUENCE: 2

Met Val Met Ala Pro Gln Pro Ser Arg Ala Leu Ser Pro Arg Leu Ser
1               5                   10                  15

Arg Ala Pro Gly Ala Gly His Ala Ser Cys Arg Cys Ser Ala Ala Leu
            20                  25                  30

Ala Pro Leu Phe Gly Lys Arg Pro Ala Pro Leu Val Val Ser Phe Pro
        35                  40                  45

Arg Ala Gly Ser Gly Gly Ala Val Ala Ser Cys Ser Ala Val Pro Val
    50                  55                  60

Gln Glu Ser Ser Thr Ser Thr Ala Val Ser Lys Lys Lys Asp Gly Ala
65                  70                  75                  80

Asn Lys Glu Ala Thr Ala Ala Lys Pro Lys Lys Ala Ala Ala Leu Pro
                85                  90                  95

Leu Pro Glu Met Met Gln Glu Glu Ile Ile Pro Pro Leu Lys Ala Ala
            100                 105                 110

Leu Glu Ala Glu Glu Asp Val Ser Gln Val Gln Leu Ala Phe Glu Asn
        115                 120                 125

Asn Thr Leu Glu Gly Ser Phe Ile Lys Asp Asp Val Pro Tyr Cys Phe
    130                 135                 140

Trp Ala Phe Phe Pro Lys Gly Asp Leu Thr Gly Pro Lys Gly Phe Ala
145                 150                 155                 160

Leu Ser Ser Tyr Ser Asn Glu Val Ser Thr Ile Glu Pro Phe Leu Ile
                165                 170                 175

Asp Glu Lys Arg Val Thr Ala Lys Tyr Val Val Phe Trp Val Tyr Lys
            180                 185                 190

Arg Leu Ala Gly Gln Gly Ile Leu Pro Val Trp Lys Glu Glu Glu Gly
        195                 200                 205
```

Glu Asp His Gln Asp Ala Lys
    210                 215

<210> SEQ ID NO 3
<211> LENGTH: 1580
<212> TYPE: DNA
<213> ORGANISM: Flaveria trinervia
<220> FEATURE:
<221> NAME/KEY: misc_feature
<222> LOCATION: (1)..(1580)
<223> OTHER INFORMATION: GLDC promoter and 5'UTR

<400> SEQUENCE: 3

```
aagctttact cctctcaact ttcaaatcat aacataaaag ttcgtaggtt tgtgttcttc      60
ccaaaaaaaa agtgattttt tttcatcggt taattcatga ttaacatttc gacattcatt     120
ccactatttc acatcatgtt ttgatgggag attgaaatag cgataaggcg aatgtgaaag     180
tgtgaaacag gatgagccac accatcacca catcacaatt tacccaaata atatcccaaa     240
gattcatacg cattttgatc cactgaaacc ccatccaatt ctatccaatg cccaccacat     300
gttcgacgat ttgcctcagt gaatcaagac caacacatgc cactgctttc tgcttttttag    360
tccctgataa caaacgattg ctttcattg ctcactgtag aaagtggaga cacccaacaa     420
ctatcatctc cacgtggttc cgtgccgcct ttttgccttt catactgctg gtgcgtcatt     480
tgtcgtcatc aaagcactca cccactatca ttgatctcga aatcttgaat ctttaggttt     540
ttatgctttg atacttgaac tctacacaca gtctcgtatc tgacttttttg ttatctgtgt    600
tttgctttac taaagatctc acctttaatc aagttttgaa cttttgatgg atttgtcatg     660
ataatgaaga acacatagtt attattgatt atattttgac gaatcttttt tcatgatcgt     720
taaacataat ttgagttctt tttaccttgt ctttctttga ggtttaactg tacatgaaga     780
ctgtattttg agtttattgc ataaatggtc tatatagttt gggttaaaac aactggtttt     840
aatatcaagt ttgatactag acaaaccaac tttttgatta acttttaaaa aaattaataa     900
gtctatttgg aaaaaaattg aaaatttgat tttaaggggt taaagttcct ttttgaaaag     960
ttaataagag taacttttga aatgtaactt ttaaaaaaat actgttgata aaaaagaaa     1020
tcctaatcat gggcttagta ttgtaagtag cttggatatt gaagctaatt tttcacttta    1080
tatttataga aaagttaatg gaagtaagag gtttggatac tttttttctt aatttagacg    1140
aatgttacac atgaaaaata agcgttgttt tgtaagattt ttttaattcg caagcactaa    1200
actcctaatc aacttttggg gttaaggagt aggcagtaaa ccaaaagcgt ttttgcacga    1260
tacgatgttc aaacatttga tctataacga taagtccaag tgcgttacaa aatgaaactt    1320
tggtatccaa tatgaaactg ggtgtgtagt tcagtaccaa aagcataact ttcagcctcc    1380
ttagtgactt atgactaggc aagagaacat gtgagcccaa tgtactaact ttttaccccct   1440
tttattacca ccaccccagc ccccaccat gaaccgatca gaaaaagaag caagaaaaac     1500
agagcattct tgctccttct tcttcatcaa ttcaataaca ttcttcatac cattagaccc    1560
catcttacac tgtttcacac                                                 1580
```

<210> SEQ ID NO 4
<211> LENGTH: 983
<212> TYPE: DNA
<213> ORGANISM: Zea mays
<220> FEATURE:
<221> NAME/KEY: misc_feature
<222> LOCATION: (1)..(983)
<223> OTHER INFORMATION: RbcS promoter and 5'UTR

```
<400> SEQUENCE: 4
gagctccctt taatctggcg ctagatctgc atccgcggct tgcaaagata aatggcacat      60
ttagtgtgtt attttgcaat acctttcata gtagatatcc ttaaatgcag ttttaggcat     120
gtttgggtaa ttaaataaca ttttaggag gagttttaga tttacctttc tttcgtgatg      180
actgatgaca gacgtgggga attcaaatgc aactctagcg aaagttcata tatttttcat     240
aaatagctga ggctgggta attatttttt ttgtagaaaa atagaatagg tggaatggtt      300
ggggaaggcg taggcgctcg tggacgacgc ccgataaaag acaagaggcg gaattgccat     360
gaattcgagg tagctaagta aggcgcatat atatgccaaa aaattctact gtcactttcc     420
aatttcaatg cgctgccaaa caagccatcc tggaaactga cttgaattca gcccaattct     480
gtagatccaa acagggccgg cgtcagtgcc tcaggtgaga gagcagcaga cgatgcaaag     540
agccaaaact gcaagcagac gcagccgaag ccgaagccga agcccaagcc caaaactgtt     600
ttgtctttgc ccagaaccgc gacgagccta aactgcgctt cctcctatct acaagtccct     660
ggcacatcac gcatagtcca accatggcgc gcaggcgata aggcgcgcca cggggacgcg     720
acatgtggtg gcggacgcga tcaggatagg gccaggctgg ccgggcgcgg ccacgggaga     780
acggtggcca ctcgtcccac atccgcttcg tcctgtcctg tactgcgtcc tgcccccaac     840
gagagccgga gccggccatc ccgtcgcaca ctctcccccct ctatatatgc cgtcggtgtg     900
ggggagccta ctacaggacg acccaagcaa gcaagcaagc agcgagtaca tacatactag     960
gcagccaggc agccgtttca cac                                             983

<210> SEQ ID NO 5
<211> LENGTH: 798
<212> TYPE: DNA
<213> ORGANISM: Zea mays
<220> FEATURE:
<221> NAME/KEY: misc_feature
<222> LOCATION: (1)..(798)
<223> OTHER INFORMATION: RbcS7A promoter

<400> SEQUENCE: 5
gatgactgat gacagacgtg gggaattcaa atgcaactct agcgaaagtt catatatttt      60
tcataaatag ctgaggctgg ggtaattatt tttttgtag aaaaatagaa taggtggaat      120
ggttggggaa ggcgtaggcg ctcgtggacg acgcccgata aaagacaaga ggcggaattg     180
ccatgaattc gaggtagcta agtaaggcgc atatatatgc caaaaaattc tactgtcact     240
ttccaatttc aatgcgctgc caaacaagcc atcctggaaa ctgacttgaa ttcagcccaa     300
ttctgtagat ccaaacaggg ccggcgtcag tgcctcaggt gagagagcag cagacgatgc     360
aaagagccaa aactgcaagc agacgcagcc gaagccgaag ccgaagccca agcccaaaac     420
tgttttgtct ttgcccagaa ccgcgacgag cctaaactgc gcttcctcct atctacaagt     480
ccctggcaca tcacgcatag tccaaccatg gcgcgcaggc gataaggcga gccacgggga     540
cgcgacatgt ggtggcggac gcgatcagga tagggccagg ctggccgggc gcggccacgg     600
gatctagatg gccactcgtc ccacatccgc ttcgtcctgt cctgtactgc gtcctgcccc     660
caacgagagc cggagccggc catcccgtcg cacactctcc cctctatat atgccgtcgg     720 tgtgggggag cctactacag gacgacccaa gcaagcaagc aagcagcgag tacatacata     780
ctaggcagcc aggcagcc                                                  798

<210> SEQ ID NO 6
<211> LENGTH: 450
```

```
<212> TYPE: DNA
<213> ORGANISM: Zea mays
<220> FEATURE:
<221> NAME/KEY: misc_feature
<222> LOCATION: (1)..(450)
<223> OTHER INFORMATION: RbcS 3'UTR

<400> SEQUENCE: 6
acacacgacc gaccgcgccc gccggccgcc ccccgccggc tagctagcta gctagctcct      60
gcgtgagcta gtagctagtg ccatgcgtcg tctctgtcgt tcggttttgc ttcgggtcac     120
cgtgtaccct ttgcttgctt ggtttcttct ttccttttt  cctttttttt tcttcttttc     180
cccggccatg gttcctttgc tttccagcag ttctctgctg gatgtgatgt atccattgtt     240
gcaatcatgg ccttgcattg gctacctcta tacctgctac aaaactactg caacgcctat     300
atatacttgg ggtgaggaac atgtgaatgc aagctccggc tatcatatac atgtaatatg     360
gatacaaact atatatataa atccgccgag gcgccgacaa tactatacga caccgtgtta     420
agttaatata taactggtgc ttttattta                                        450

<210> SEQ ID NO 7
<211> LENGTH: 219
<212> TYPE: PRT
<213> ORGANISM: Sorghum bicolor
<220> FEATURE:
<221> NAME/KEY: MISC_FEATURE
<222> LOCATION: (1)..(219)
<223> OTHER INFORMATION: DUF2996 domain-containing protein

<400> SEQUENCE: 7

Met Val Met Ala Pro Gln Pro Leu Arg Ala Leu Arg Pro Ser Ala Pro
1               5                   10                  15

Ala Ala Gly His Ala Ala Cys Arg Cys Ser Ala Ala Pro Leu Phe
            20                  25                  30

Gly Lys Arg Ala Pro Leu Val Val Ala Phe Pro Arg Ala Gly Ser Gly
        35                  40                  45

Gly Gly Ala Val Val Val Ser Cys Ser Ala Val Gln Glu Ser Ser Thr
    50                  55                  60

Ser Thr Thr Val Ser Lys Lys Asp Ala Ala Asp Gly Ala Lys Glu
65                  70                  75                  80

Ala Thr Ala Ala Ala Lys Pro Ala Ala Ala Lys Pro Lys Lys
                85                  90                  95

Ala Ala Ala Leu Pro Leu Pro Glu Met Met Gln Gln Glu Ile Ile Pro
            100                 105                 110

Pro Leu Lys Ala Ala Leu Glu Ala Glu Asp Val Ser Gln Val Glu
        115                 120                 125

Leu Ala Phe Gln Asn Asn Thr Leu Glu Gly Ser Phe Ile Lys Asn Asp
    130                 135                 140

Val Pro Tyr Tyr Phe Trp Ala Phe Phe Pro Lys Gly Asp Leu Thr Gly
145                 150                 155                 160

Pro Lys Gly Phe Ala Leu Ser Ser Tyr Ser Asn Glu Val Ser Thr Ile
                165                 170                 175

Glu Pro Phe Leu Ile Asp Glu Lys Arg Ile Thr Ala Lys Tyr Val Val
            180                 185                 190

Phe Trp Val Tyr Lys Arg Leu Ala Gly Gln Gly Ile Leu Pro Val Trp
        195                 200                 205

Lys Glu Glu Glu Gly Glu Glu Glu Asp Ala Lys
    210                 215
```

<210> SEQ ID NO 8
<211> LENGTH: 215
<212> TYPE: PRT
<213> ORGANISM: Panicum hallii
<220> FEATURE:
<221> NAME/KEY: MISC_FEATURE
<222> LOCATION: (1)..(215)
<223> OTHER INFORMATION: DUF2996 domain-containing protein

<400> SEQUENCE: 8

Met Ala Pro Gln Pro Leu His Thr Leu Arg Leu Ser Thr Pro Ala Gly
1               5                   10                  15

His Ala Val Cys Arg Cys Ser Ala Ala Pro Ile Phe Gly Lys Arg Leu
            20                  25                  30

Pro Ala Ile Val Ala Phe Pro Arg Ala Gly Ser Gly Gly Ala Val Val
        35                  40                  45

Leu Cys Ser Ala Val Gln Glu Ser Ser Thr Ser Thr Thr Val Ser Lys
    50                  55                  60

Lys Lys Asp Ala Ala Asp Gly Glu Lys Glu Ala Thr Ala Ala Ala
65                  70                  75                  80

Ala Lys Pro Ala Ala Ala Lys Pro Lys Lys Ala Pro Ala Lys Pro
                85                  90                  95

Leu Pro Glu Met Met Gln Glu Ile Ile Pro Pro Leu Lys Val Ala
            100                 105                 110

Leu Glu Ala Glu Glu Asn Val Ser Gln Val Gln Leu Ser Phe Gln Asn
        115                 120                 125

Asn Thr Leu Glu Gly Ser Phe Ile Lys Asp Asp Val Pro Tyr Tyr Phe
130                 135                 140

Trp Ala Phe Phe Pro Lys Gly Asp Leu Thr Gly Pro Lys Gly Phe Ala
145                 150                 155                 160

Leu Ser Ser Tyr Ser Asn Glu Val Ser Thr Ile Glu Pro Phe Leu Val
                165                 170                 175

Asp Glu Lys Arg Val Thr Ala Gln Tyr Val Val Phe Trp Val Tyr Lys
            180                 185                 190

Arg Leu Ala Gly Gln Gly Ile Leu Pro Val Trp Lys Glu Glu Glu Gly
        195                 200                 205

Gly Glu Glu Glu Gly Ala Lys
    210                 215

<210> SEQ ID NO 9
<211> LENGTH: 216
<212> TYPE: PRT
<213> ORGANISM: Dichanthelium oligosanthes
<220> FEATURE:
<221> NAME/KEY: MISC_FEATURE
<222> LOCATION: (1)..(216)
<223> OTHER INFORMATION: DUF2996 domain-containing protein

<400> SEQUENCE: 9

Met Ala Pro Gln Pro Leu His Thr Leu Arg Leu Ser Ala Pro Ala Gly
1               5                   10                  15

His Ala Ala Val Cys Arg Cys Ser Ala Ala Pro Leu Phe Gly Lys Arg
            20                  25                  30

Leu Pro Ala Ile Val Ala Phe Pro Arg Ala Gly Ser Gly Gly Ala Val
        35                  40                  45

Val Phe Cys Ser Ala Val Gln Gln Glu Ser Ser Thr Ser Thr Thr Val
    50                  55                  60

Ser Glu Lys Lys Asp Ala Ala Glu Gly Glu Lys Lys Glu Ala Thr Ala

```
                65                  70                  75                  80
Ala Ala Ala Lys Pro Ala Ala Ala Lys Pro Lys Lys Ala Pro Ala
                    85                  90                  95

Lys Pro Leu Pro Glu Met Met Gln Glu Ile Ile Pro Pro Leu Lys
                100                 105                 110

Asp Ala Leu Glu Ala Glu Glu Asn Val Ser Gln Val Gln Leu Ser Phe
                115                 120                 125

Gln Asn Asn Thr Leu Glu Gly Ser Phe Ile Lys Asp Asp Val Pro Tyr
                130                 135                 140

Tyr Phe Trp Ala Phe Phe Pro Lys Gly Asp Leu Thr Gly Pro Lys Gly
145                 150                 155                 160

Phe Ala Leu Ser Ser Tyr Ser Asn Glu Val Ser Thr Ile Glu Pro Phe
                165                 170                 175

Leu Ile Asp Glu Lys Arg Ile Thr Ser Lys Tyr Val Val Phe Trp Val
                180                 185                 190

Tyr Lys Arg Leu Ala Gly Gln Gly Ile Leu Pro Val Trp Lys Glu Glu
                195                 200                 205

Glu Gly Glu Glu Glu Ala Ala Lys
    210                 215

<210> SEQ ID NO 10
<211> LENGTH: 220
<212> TYPE: PRT
<213> ORGANISM: Setaria italica
<220> FEATURE:
<221> NAME/KEY: MISC_FEATURE
<222> LOCATION: (1)..(220)
<223> OTHER INFORMATION: DUF2996 domain-containing protein

<400> SEQUENCE: 10

Met Ala Pro Pro Gln Pro Leu Arg Thr Leu Arg Leu Ser Ala Pro Ala
1               5                   10                  15

Gly His Ala Ala Val Cys Arg Cys Ser Ala Ala Pro Leu Phe Gly Lys
                20                  25                  30

Arg Leu Pro Ala Ile Val Ala Phe Pro Arg Ala Gly Ser Gly Gly Ala
            35                  40                  45

Val Ala Leu Cys Ser Ala Val Gln Gln Glu Ser Ser Thr Ser Thr Thr
50                  55                  60

Val Ser Lys Lys Lys Asp Ala Asp Gly Glu Lys Lys Glu Ala Thr
65                  70                  75                  80

Ala Ala Ala Ala Ala Lys Pro Ala Ala Ala Lys Pro Lys Lys Ala
                85                  90                  95

Pro Ala Lys Pro Leu Pro Glu Met Met Gln Glu Glu Ile Ile Pro Pro
                100                 105                 110

Leu Lys Asp Ala Leu Glu Ala Glu Glu Asn Val Ser Gln Val Gln Leu
                115                 120                 125

Ser Phe Gln Asn Asn Thr Leu Glu Gly Ser Phe Ile Lys Asp Asp Val
                130                 135                 140

Pro Tyr Tyr Phe Trp Ala Phe Phe Pro Lys Gly Asp Leu Thr Gly Pro
145                 150                 155                 160

Lys Gly Phe Ala Leu Ser Ser Tyr Ser Asn Glu Val Ser Thr Ile Glu
                165                 170                 175

Pro Phe Leu Ile Asp Glu Lys Arg Ile Thr Ser Gln Tyr Val Val Phe
                180                 185                 190

Trp Val Tyr Lys Arg Leu Ala Gly Gln Gly Ile Leu Pro Val Trp Lys
                195                 200                 205
```

```
Glu Glu Glu Gly Glu Glu Ala Ala Gly Ala Lys
    210             215             220

<210> SEQ ID NO 11
<211> LENGTH: 228
<212> TYPE: PRT
<213> ORGANISM: Oryza sativa
<220> FEATURE:
<221> NAME/KEY: MISC_FEATURE
<222> LOCATION: (1)..(228)
<223> OTHER INFORMATION: DUF2996 domain-containing protein

<400> SEQUENCE: 11

Met Ala Ser Gln Pro Leu Arg Leu Val Arg Pro Ser Pro Leu Ala Gly
1               5                   10                  15

Arg His Ala Ala Ala Cys Lys Cys Ser Ala Ala Ile Pro Leu Val Phe
            20                  25                  30

Gly Arg Gln Arg Leu Pro Leu Leu Val Ala Phe Pro Arg Gly Ser Gly
        35                  40                  45

Ser Gly Ser Gly Ser Gly Ala Ser Cys Ser Ala Val Gln Glu Ser Ser
    50                  55                  60

Ser Ala Ala Ala Ala Thr Thr Val Ser Glu Lys Lys Asp Ala Ala Asp
65                  70                  75                  80

Ala Lys Lys Glu Ala Thr Ala Glu Ala Lys Pro Ala Ala Lys Pro Ala
                85                  90                  95

Ala Lys Pro Lys Lys Pro Pro Val Lys Pro Leu Pro Glu Met Met Gln
            100                 105                 110

Glu Glu Ile Ile Pro Pro Leu Lys Ala Ala Leu Glu Ala Glu Asp Asp
        115                 120                 125

Val Ser Gln Val Glu Leu Ser Phe Glu Asp Asn Arg Leu Glu Gly Ser
    130                 135                 140

Phe Ile Lys Asp Glu Val Pro Tyr Tyr Phe Trp Ala Phe Phe Pro Asn
145                 150                 155                 160

Gly Asp Leu Thr Gly Pro Lys Gly Phe Ala Leu Ser Ser Tyr Ser Thr
                165                 170                 175

Glu Val Ser Thr Ile Glu Pro Phe Leu Ile Asp Glu Lys Arg Ala Asn
            180                 185                 190

Ala Lys Tyr Val Val Phe Trp Val Tyr Lys Arg Leu Ala Gly Gln Gly
        195                 200                 205

Ile Leu Pro Val Trp Lys Glu Glu Gly Glu Gly Glu Gly Glu Gly
    210                 215                 220

Glu Ser Ser Ala
225

<210> SEQ ID NO 12
<211> LENGTH: 220
<212> TYPE: PRT
<213> ORGANISM: Hordeum vulgare
<220> FEATURE:
<221> NAME/KEY: MISC_FEATURE
<222> LOCATION: (1)..(220)
<223> OTHER INFORMATION: DUF2996 domain-containing protein

<400> SEQUENCE: 12

Met Ala Thr Arg Ala Leu His Ser Pro Arg Leu Thr Ser Pro Pro Leu
1               5                   10                  15

Thr Gly Arg His Ala Ala Thr Arg Cys Lys Cys Ser Ala Ala Pro Leu
            20                  25                  30
```

```
Phe Ala Lys Arg Leu Pro Leu Val Val Ala Phe Pro Arg Ser Val Ala
            35                  40                  45

Ser Cys Cys Ala Val Gln Glu Ser Ser Ala Gly Ala Thr Ala Ala Ala
 50                  55                  60

Ala Thr Ala Val Ser Glu Thr Lys Asp Ala Asp Gly Asp Lys Lys Glu
 65                  70                  75                  80

Ala Ala Ala Ala Glu Ala Lys Pro Ala Ala Lys Pro Ala Ala Ala Lys
                 85                  90                  95

Pro Lys Lys Ala Pro Pro Lys Pro Leu Pro Glu Met Met Glu Glu Glu
                100                 105                 110

Ile Ile Pro Pro Leu Lys Thr Ala Leu Glu Ala Glu Glu Asp Val Ser
                115                 120                 125

Gln Val Val Leu Thr Phe Gln Asn Asn Thr Leu Glu Gly Ser Phe Val
130                 135                 140

Lys Glu Asp Ile Pro Tyr Tyr Phe Trp Ala Phe Pro Gln Gly Asp
145                 150                 155                 160

Leu Thr Gly Pro Lys Gly Phe Ala Met Thr Ser Tyr Ser Met Glu Val
                165                 170                 175

Ser Thr Ile Glu Pro Phe Leu Ile Asp Glu Lys Arg Val Thr Pro Gln
                180                 185                 190

Tyr Val Val Phe Trp Val Tyr Lys Arg Leu Ala Gly Gln Gly Val Leu
                195                 200                 205

Pro Val Trp Lys Ala Glu Asp Leu Thr Pro Ala Gln
                210                 215                 220

<210> SEQ ID NO 13
<211> LENGTH: 269
<212> TYPE: PRT
<213> ORGANISM: Aegilops tauschii
<220> FEATURE:
<221> NAME/KEY: MISC_FEATURE
<222> LOCATION: (1)..(269)
<223> OTHER INFORMATION: DUF2996 domain-containing protein

<400> SEQUENCE: 13

Met Leu His Arg Ser Leu Leu His Arg Ala Ala Glu Ala Ala Asp Arg
 1               5                  10                  15

Ala Ala Ser Ala Gln Arg His Pro Thr Gln Pro Val Asp Ser Ser Asp
                 20                  25                  30

Pro Ser Thr Gly Arg Arg Ser Ala Ala Arg Gln Thr Arg Pro Met
             35                  40                  45

Ala Thr Arg Ala Leu His Ser Pro Arg Leu Thr Ser Pro Pro Leu Thr
 50                  55                  60

Gly Arg His Ala Ala Arg Cys Lys Cys Ser Ala Ala Pro Leu Phe
 65                  70                  75                  80

Ala Lys Arg Leu Pro Leu Val Val Ala Phe Pro Arg Ser Val Ala Ser
                 85                  90                  95

Cys Cys Ala Val Gln Glu Ser Ser Ala Gly Ala Ala Ala Ala Ala
                100                 105                 110

Thr Thr Val Ser Glu Thr Lys Asp Ala Gly Gly Asp Lys Lys Glu Ala
                115                 120                 125

Ala Ala Ala Glu Ala Lys Pro Ala Ala Lys Pro Ala Ala Ala Lys Pro
                130                 135                 140

Lys Lys Ala Pro Pro Lys Pro Leu Pro Glu Met Met Glu Glu Glu Ile
145                 150                 155                 160

Ile Pro Pro Leu Lys Thr Ala Leu Glu Ala Glu Glu Asp Val Ser Gln
```

```
                165                 170                 175
Val Val Leu Thr Phe Gln Asn Asn Thr Leu Glu Gly Ser Phe Val Lys
            180                 185                 190

Glu Asp Ile Pro Tyr Tyr Phe Trp Ala Phe Phe Pro Gln Gly Asp Leu
        195                 200                 205

Thr Gly Pro Lys Gly Phe Ala Met Thr Ser Tyr Ser Met Glu Val Ser
    210                 215                 220

Thr Ile Glu Pro Phe Leu Ile Asp Glu Lys Arg Ile Thr Pro Gln Tyr
225                 230                 235                 240

Val Val Phe Trp Val His Lys Arg Leu Ala Gly Gln Gly Val Leu Pro
                245                 250                 255

Val Trp Arg Ala Glu Asp Leu Ser Pro Ala Pro Ala Glu
            260                 265

<210> SEQ ID NO 14
<211> LENGTH: 221
<212> TYPE: PRT
<213> ORGANISM: Oryza brachyantha
<220> FEATURE:
<221> NAME/KEY: MISC_FEATURE
<222> LOCATION: (1)..(221)
<223> OTHER INFORMATION: DUF2996 domain-containing protein

<400> SEQUENCE: 14

Met Ala Ala Thr Gln Pro Leu Arg Leu Val Arg Pro Thr Pro Leu Ala
1               5                   10                  15

Arg Gly Arg Cys Lys Cys Ser Ala Ala Val Pro Leu Val Phe Gly Arg
            20                  25                  30

Gln Arg Leu Pro Leu Leu Val Ala Phe Pro Arg Gly Ser Gly Ser Gly
        35                  40                  45

Ala Ser Cys Ser Ala Val Gln Glu Ser Ser Ala Ala Ala Ala Ala Thr
    50                  55                  60

Thr Val Ser Glu Lys Lys Asp Ala Ala Asp Lys Lys Glu Ala Thr
65                  70                  75                  80

Ala Glu Ala Lys Pro Ala Ala Ser Lys Pro Ala Ala Lys Pro Lys Lys
                85                  90                  95

Pro Pro Val Lys Ala Leu Pro Glu Met Met Gln Glu Ile Ile Pro
            100                 105                 110

Pro Leu Met Ala Ala Leu Glu Ala Glu Asp Asp Val Ser Gln Val Glu
        115                 120                 125

Leu Ser Phe Gln Asp Asn Arg Leu Glu Gly Ser Phe Val Lys Asp Asp
    130                 135                 140

Val Pro Tyr Tyr Phe Trp Ala Phe Phe Pro Asn Gly Asp Leu Thr Gly
145                 150                 155                 160

Pro Lys Gly Phe Ala Leu Ser Ser Tyr Ala Thr Glu Val Ser Thr Ile
                165                 170                 175

Glu Pro Phe Leu Ile Asp Glu Lys Arg Ala Asn Ala Lys Tyr Val Val
            180                 185                 190

Phe Trp Val Tyr Lys Arg Leu Ala Gly Gln Gly Ile Leu Pro Val Trp
        195                 200                 205

Lys Glu Glu Glu Gly Glu Gly Glu Ser Ala Glu
    210                 215                 220

<210> SEQ ID NO 15
<211> LENGTH: 218
<212> TYPE: PRT
<213> ORGANISM: Brachypodium distachyon
```

```
<220> FEATURE:
<221> NAME/KEY: MISC_FEATURE
<222> LOCATION: (1)..(218)
<223> OTHER INFORMATION: DUF2996 domain-containing protein

<400> SEQUENCE: 15

Met Ala Pro Gln Ala Leu Arg Leu Leu Arg Leu Thr Thr Pro Leu Gly
1               5                   10                  15

Pro Arg Gly Gly His His Ala Pro Pro Leu Phe Ala Lys Arg Leu Pro
            20                  25                  30

Leu Val Val Ala Phe Pro Arg Gly Ala Gly Ala Ser Cys Ser Ala Val
        35                  40                  45

Gln Glu Ser Ser Ala Ala Ala Ala Thr Thr Val Ser Glu Lys Lys
50                  55                  60

Asp Ala Asp Gly Asp Asn Lys Glu Ala Ala Glu Ala Lys Pro Ala
65                  70                  75                  80

Ala Lys Pro Ala Ala Ala Ala Lys Leu Lys Lys Pro Pro Lys
                85                  90                  95

Pro Leu Pro Glu Met Met Glu Glu Glu Ile Ile Pro Pro Leu Lys Ala
            100                 105                 110

Ala Leu Glu Gly Glu Glu Asp Val Ser Gln Val Glu Leu Ser Phe Gln
        115                 120                 125

Asn Asn Thr Leu Glu Gly Ser Phe Gln Lys Lys Asp Ile Pro Tyr Tyr
130                 135                 140

Phe Trp Ala Phe Phe Pro Gln Gly Asp Leu Thr Gly Pro Lys Gly Phe
145                 150                 155                 160

Ala Met Thr Ser Tyr Ser Met Glu Val Ser Thr Ile Glu Pro Phe Leu
                165                 170                 175

Val Asp Glu Lys Arg Val Thr Pro Gln Tyr Val Val Phe Trp Val Tyr
            180                 185                 190

Lys Arg Leu Ala Gly Gln Gly Ile Leu Pro Val Trp Lys Glu Glu Asp
        195                 200                 205

Leu Asn Pro Glu Pro Ser Thr Val Ala Lys
210                 215

<210> SEQ ID NO 16
<211> LENGTH: 212
<212> TYPE: PRT
<213> ORGANISM: Asparagus officinalis
<220> FEATURE:
<221> NAME/KEY: MISC_FEATURE
<222> LOCATION: (1)..(212)
<223> OTHER INFORMATION: DUF2996 domain-containing protein

<400> SEQUENCE: 16

Met Ala Cys Arg Ser Ile Asn Met Tyr Gly Ser Leu Leu Arg Pro Arg
1               5                   10                  15

Arg Ile Ile Ala Asp Gln Ser Pro Val Ile Ser Phe Arg Pro Asn Glu
            20                  25                  30

Ala Gly Arg Leu Gly Val Asn Arg Val Val Leu Cys Cys Ser Ala
        35                  40                  45

Pro Glu Ser Ser Ser Thr Ala Thr Val Thr Asp Lys Lys Glu Ala Glu
50                  55                  60

Pro Ala Lys Ala Thr Thr Pro Ala Ala Ala Thr Ala Thr Glu
65                  70                  75                  80

Lys Lys Glu Ala Glu Pro Ala Lys Ala Lys Ala Ser Pro Ala Lys Pro
                85                  90                  95
```

-continued

```
Lys Lys Ala Pro Val Lys Pro Leu Pro Glu Met Met Glu Glu Asp Val
            100                 105                 110

Ile Pro Ser Leu Lys Ala Thr Leu Glu Thr Glu Glu Asp Leu Ser Gln
        115                 120                 125

Ile Glu Leu Ser Phe Lys Asp Asn Arg Leu Glu Gly Ser Phe Leu Lys
    130                 135                 140

Lys Asp Val Pro Tyr Tyr Phe Trp Ala Phe Phe Pro Asp Gly Val Leu
145                 150                 155                 160

Thr Gly Pro Lys Gly Phe Ser Leu Ser Ser His Gly Ser Glu Ala Ser
                165                 170                 175

Thr Val Glu Pro Phe Leu Ile Asp Glu Arg Lys Ile Thr Ala Lys His
            180                 185                 190

Ile Val Phe Trp Val Glu Lys Arg Leu Ala Ala Gln Gly Ile Leu Pro
        195                 200                 205

Val Trp Lys Glu
    210
```

<210> SEQ ID NO 17
<211> LENGTH: 201
<212> TYPE: PRT
<213> ORGANISM: Musa acuminata
<220> FEATURE:
<221> NAME/KEY: MISC_FEATURE
<222> LOCATION: (1)..(201)
<223> OTHER INFORMATION: DUF2996 domain-containing protein

<400> SEQUENCE: 17

```
Met Ala Cys Gln Ser Ile Asn Ile His Ser Ala Leu Thr Arg Gln Val
1               5                   10                  15

Met Asp Ala Ser Phe Ser Ile Phe Ser Arg Ala Ser Met Val Gly Tyr
            20                  25                  30

Arg Arg Gln Glu Pro Gly Arg Ile Met Leu Thr His Gly Thr Val Val
        35                  40                  45

Cys Ser Ala Ile Gln Glu Ser Ser Thr Ala Ala Val Thr Asp Val Lys
    50                  55                  60

Lys Gln Glu Val Ala Thr Lys Ala Glu Ala Pro Ala Ala Ala Asn Asp
65                  70                  75                  80

Ala Pro Gly Lys Pro Lys Pro Pro Val Arg Pro Leu Pro Glu Met
                85                  90                  95

Met Glu Glu Glu Val Ile Pro Ser Leu Lys Glu Cys Leu Glu Ala Gln
            100                 105                 110

Glu Asp Val Ser Glu Ile Glu Ile Ser Phe Gln Asp Asn Arg Leu Glu
        115                 120                 125

Gly Ser Phe Leu Lys Lys Gly Ile Pro Tyr Ser Phe Trp Ala Phe Phe
    130                 135                 140

Pro Asn Gly Val Leu Thr Gly Pro Lys Gly Phe Ser Leu Ser Ser Tyr
145                 150                 155                 160

Gly Ser Gly Val Ser Thr Val Glu Pro Phe Leu Ile Asp Glu Lys Arg
                165                 170                 175

Ile Asn Ala Lys Leu Val Val Phe Trp Val Lys Lys Arg Leu Ala Ala
            180                 185                 190

Gln Gly Ile Leu Pro Val Trp Thr Glu
        195                 200
```

<210> SEQ ID NO 18
<211> LENGTH: 212
<212> TYPE: PRT

<213> ORGANISM: Ananas comosus
<220> FEATURE:
<221> NAME/KEY: MISC_FEATURE
<222> LOCATION: (1)..(212)
<223> OTHER INFORMATION: DUF2996 domain-containing protein

<400> SEQUENCE: 18

Met Ala Ser Gln Ser Leu Asn Thr Phe Ser Pro Leu Thr His His
1               5                   10                  15

Leu Arg Arg Lys Ile Leu Pro Phe Phe Ala Asn Ser Pro Ala Val Gly
            20                  25                  30

Asp Arg Arg Ile Glu Pro Lys Lys Cys Arg Phe Ser Arg Arg Cys Ala
        35                  40                  45

Val Ile Ser Ser Ala Val Gln Glu Ser Ser Thr Ala Ile Val Thr Asp
    50                  55                  60

Lys Glu Gly Gly Glu Ala Glu Ala Glu Ser Lys Ala Ala Thr
65                  70                  75                  80

Pro Ala Ala Lys Ala Val Pro Gly Lys Ala Lys Lys Ala Pro Ala Lys
                85                  90                  95

Ala Leu Pro Glu Leu Met Glu Glu Val Ile Pro Ala Leu Arg Ser
            100                 105                 110

Thr Leu Glu Ala Gln Glu Asp Val Ser Gln Val Glu Leu Ser Phe Gln
        115                 120                 125

Asp Asn Arg Leu Glu Gly Ser Phe Leu Lys Asn Asn Ile Pro Tyr Cys
    130                 135                 140

Phe Trp Ala Phe Phe Pro Asn Gly Val Leu Thr Gly Pro Lys Gly Phe
145                 150                 155                 160

Ser Leu Ser Ser Tyr Gly Ser Val Pro Ser Thr Val Glu Pro Phe Leu
                165                 170                 175

Ile Asp Glu Lys Arg Ile Thr Ala Arg His Val Val Phe Trp Val Glu
            180                 185                 190

Lys Arg Leu Ala Ala Gln Gly Ile Leu Pro Val Trp Lys Gly Glu Glu
        195                 200                 205

Ser Glu Glu Lys
    210

<210> SEQ ID NO 19
<211> LENGTH: 199
<212> TYPE: PRT
<213> ORGANISM: Jatropha curcas
<220> FEATURE:
<221> NAME/KEY: MISC_FEATURE
<222> LOCATION: (1)..(199)
<223> OTHER INFORMATION: DUF2996 domain-containing protein

<400> SEQUENCE: 19

Met Ala Thr Gln Gly Gly Ala Met Gly Val Ser Ser Phe Pro Ser Ser
1               5                   10                  15

Pro Ser Tyr Phe Ser Arg Asn Ser Arg Thr Asn Ser Ser Thr Phe Cys
            20                  25                  30

Leu His Ile Ala Ile Lys Ser Ala Thr Ser Arg Arg Ile Ser Cys
        35                  40                  45

Ser Ala Val Gln Glu Ser Ser Thr Ser Thr Val Ala Ser Asp Lys Val
    50                  55                  60

Glu Glu Lys Ala Val Lys Lys Val Glu Lys Ala Ala Ala Pro Lys
65                  70                  75                  80

Arg Lys Pro Ala Lys Glu Pro Val Lys Pro Leu Pro Gln Leu Met Glu
                85                  90                  95

Glu Asp Val Ile Pro Ser Leu Lys Ala Ile Leu Glu Thr Lys Glu Asp
                100                 105                 110

Val Thr Glu Leu Glu Leu Thr Phe Gln Asp Asn Arg Leu Glu Gly Ser
            115                 120                 125

Phe Lys Lys Gly Asn Pro Tyr Ser Phe Trp Ala Phe Phe Pro Asn
    130                 135                 140

Gly Asp Leu Thr Gly Pro Lys Gly Phe Ser Leu Ser Ser Tyr Gly Ser
145                 150                 155                 160

Glu Ala Ser Asn Val Glu Pro Phe Leu Val Asp Lys Lys Ile Thr
                165                 170                 175

Ala Lys Leu Ile Val Phe Trp Val Glu Lys Arg Leu Ala Ala Gln Gly
            180                 185                 190

Ile Ile Pro Val Trp Asp Lys
        195

<210> SEQ ID NO 20
<211> LENGTH: 212
<212> TYPE: PRT
<213> ORGANISM: Medicago truncatula
<220> FEATURE:
<221> NAME/KEY: MISC_FEATURE
<222> LOCATION: (1)..(212)
<223> OTHER INFORMATION: DUF2996 domain-containing protein

<400> SEQUENCE: 20

Met Gln Met Ala Leu Leu Leu Arg Gly Gly Ala Leu Gly Asp Ser Ser
1               5                   10                  15

Phe Arg Leu Cys Ser Leu Thr Ser Thr Ser Ser Ser Leu His Val Ser
                20                  25                  30

Gln Asn Val Val Ile Pro Asn Ser Thr Ser Ser Pro Ile Leu Pro Leu
            35                  40                  45

Ile Ala Ser Arg Phe Lys Ala Val Ser Arg Asn Lys Ile Thr Cys Ser
50                  55                  60

Ala Val Gln Glu Ser Ser Thr Ser Thr Ser Ala Thr Ala Glu Thr Lys
65                  70                  75                  80

Glu Glu Val Lys Glu Gly Ala Pro Lys Ala Ala Val Lys Lys Thr
                85                  90                  95

Pro Ala Lys Ala Pro Val Lys Pro Leu Pro Gln Met Met Glu Glu Asp
            100                 105                 110

Val Ile Pro Ser Leu Lys Ala Ile Leu Glu Ala Gln Gln Asp Leu Ser
        115                 120                 125

Asp Ile Glu Leu Val Phe Gln Asp Asn Lys Leu Glu Gly Ser Phe Leu
    130                 135                 140

Lys Lys Gly Asn Pro Tyr Ser Phe Trp Ala Phe Phe Pro Thr Gly Leu
145                 150                 155                 160

Thr Gly Pro Lys Gly Phe Ser Leu Ser Ser Tyr Asn Ser Gly Ala Ser
                165                 170                 175

Thr Val Glu Pro Phe Leu Val Asp Glu Lys Val Asn Ser Lys Leu
            180                 185                 190

Ile Val Phe Trp Val Glu Lys Arg Leu Ala Ala Gln Gly Ile Ile Pro
        195                 200                 205

Val Trp Lys Asp
    210

<210> SEQ ID NO 21
<211> LENGTH: 210

```
<212> TYPE: PRT
<213> ORGANISM: Morus notabilis
<220> FEATURE:
<221> NAME/KEY: MISC_FEATURE
<222> LOCATION: (1)..(210)
<223> OTHER INFORMATION: DUF2996 domain-containing protein

<400> SEQUENCE: 21

Met Ala Met Met Leu Gly Gly His Gly Arg Ser Thr Ile Gly Ala Ser
1               5                   10                  15

Ser Leu Ile Pro Ser Thr Ser Ser Ser Ser His Leu Thr His Gln
            20                  25                  30

Asn Ala Lys Pro Thr Ser Leu Gln Lys Gln Asn Ile Val Ile Met Asn
        35                  40                  45

Lys Leu Val Thr Leu Arg Ser Ser Ile Asn Tyr Val Val Ala Cys Ser
    50                  55                  60

Ala Val Gln Glu Ser Ser Thr Ser Thr Ala Val Ala Ala Asp Ala Asn
65                  70                  75                  80

Lys Glu Val Lys Ala Ala Pro Lys Pro Lys Pro Lys Ala Pro Ala Lys
                85                  90                  95

Ala Pro Ala Lys Pro Leu Pro Gln Met Met Glu Glu Asp Val Ile Pro
            100                 105                 110

Ser Leu Lys Ser Ile Leu Glu Ala Gln Gln Asp Leu Thr Asp Ile Gln
        115                 120                 125

Leu Ser Phe Gln Asp Asn Arg Leu Glu Gly Ser Phe Val Lys Lys Gly
    130                 135                 140

Asn Pro Tyr Ser Phe Trp Ala Phe Phe Pro Asn Gly Val Leu Thr Gly
145                 150                 155                 160

Pro Lys Gly Phe Ser Leu Ser Ser Tyr Gly Trp Gly Ala Ser Thr Val
                165                 170                 175

Glu Pro Phe Leu Ile Asp Glu Lys Lys Ile Thr Ala Lys His Val Val
            180                 185                 190

Phe Trp Val Lys Lys Arg Leu Ala Ala Gln Gly Ile Ile Pro Val Trp
        195                 200                 205

Glu Asp
    210

<210> SEQ ID NO 22
<211> LENGTH: 201
<212> TYPE: PRT
<213> ORGANISM: Hevea brasiliensis
<220> FEATURE:
<221> NAME/KEY: MISC_FEATURE
<222> LOCATION: (1)..(201)
<223> OTHER INFORMATION: DUF2996 domain-containing protein

<400> SEQUENCE: 22

Met Asn Ser Ile Phe Asn Asn Met Ala Thr Arg Gly Gly Ala Met Gly
1               5                   10                  15

Val Ser Ser Phe Pro Ser Thr Pro Ser Cys Phe Cys Arg Asn Gly Arg
            20                  25                  30

Thr Thr Cys Ser Thr Leu Ser Leu Ile Ala Ser Lys Ser Ala Thr Ser
        35                  40                  45

Arg Arg Ser Ile Thr Cys Ser Ala Val Gln Glu Ser Thr Ser Thr
    50                  55                  60

Val Glu Glu Lys Lys Val Lys Val Glu Glu Thr Ala Pro Ala Lys
65                  70                  75                  80

Pro Lys Ser Ala Gly Lys Ala Pro Ala Lys Ala Leu Pro Gln Leu Met
```

```
                    85                  90                  95
Glu Glu Asp Val Ile Pro Ser Leu Lys Ala Ile Leu Glu Ala Glu Gln
                100                 105                 110

Asp Ile Thr Glu Leu Glu Leu Ser Phe Gln Asp Asn Arg Leu Asp Gly
            115                 120                 125

Tyr Phe Lys Lys Gly Asn Pro Tyr Ser Phe Trp Ala Phe Phe Pro
        130                 135                 140

Ser Gly Asn Val Thr Gly Pro Lys Gly Phe Ser Leu Ser Ser Tyr Gly
145                 150                 155                 160

Ser Gly Ala Ser Thr Val Glu Pro Phe Leu Val Asp Glu Lys Lys Ile
                165                 170                 175

Thr Ala Lys His Val Val Phe Trp Val Glu Lys Arg Leu Ala Ala Gln
                180                 185                 190

Gly Ile Ile Pro Val Trp Lys Glu Gln
                195                 200

<210> SEQ ID NO 23
<211> LENGTH: 212
<212> TYPE: PRT
<213> ORGANISM: Trifolium pratense
<220> FEATURE:
<221> NAME/KEY: MISC_FEATURE
<222> LOCATION: (1)..(212)
<223> OTHER INFORMATION: DUF2996 domain-containing protein

<400> SEQUENCE: 23

Met Gln Met Ala Leu Leu Leu Arg Gly Gly Thr Val Gly Asp Ser Ser
1               5                   10                  15

Phe Arg Leu Cys Ser Leu Lys Ser Thr Ser Ser Ser Leu His Val Ser
                20                  25                  30

Gln Asn Val Val Ile Pro Asn Ser Ser Ser Pro Ile Leu Pro Leu
            35                  40                  45

Ile Ala Ser Arg Phe Lys Thr Ile Ser Arg Asn Lys Ile Ile Cys Ser
        50                  55                  60

Ala Val Gln Glu Ser Ser Thr Ser Thr Ser Ala Thr Ala Glu Thr Lys
65                  70                  75                  80

Glu Glu Val Lys Ala Ala Pro Lys Ala Ala Thr Glu Lys Lys Ala Pro
                85                  90                  95

Ala Ala Lys Ala Pro Val Lys Pro Leu Pro Gln Met Met Glu Glu Asp
                100                 105                 110

Val Ile Pro Ser Leu Lys Ala Ile Leu Glu Ala Gln Gln Asp Leu Ser
            115                 120                 125

Asp Leu Gln Leu Val Phe Gln Asp Asn Lys Leu Glu Gly Ser Phe Ser
        130                 135                 140

Lys Lys Gly Asn Pro Tyr Ser Phe Trp Ala Phe Phe Pro Thr Gly Leu
145                 150                 155                 160

Thr Gly Pro Lys Gly Phe Ser Leu Ser Ser Tyr Asn Ser Gly Ala Ser
                165                 170                 175

Thr Val Glu Pro Phe Leu Val Asp Glu Lys Lys Val Thr Ala Lys Leu
                180                 185                 190

Ile Val Phe Trp Val Glu Lys Arg Leu Ala Ala Gln Gly Ile Ile Pro
            195                 200                 205

Val Trp Lys Asp
    210

<210> SEQ ID NO 24
```

```
<211> LENGTH: 201
<212> TYPE: PRT
<213> ORGANISM: Phoenix dactylifera
<220> FEATURE:
<221> NAME/KEY: MISC_FEATURE
<222> LOCATION: (1)..(201)
<223> OTHER INFORMATION: DUF2996 domain-containing protein

<400> SEQUENCE: 24
```

Met Ala Ser Gln Ser Leu Asn Val Tyr Ser Pro Leu Thr Arg Gln Val
1               5                   10                  15

Lys Gly Asp Thr Val Pro Val Phe Ser Lys Ala Pro Val Thr Ser Asp
            20                  25                  30

Arg Arg His Lys His Gly Arg Ile Val Leu Ser Arg Gly Ser Val Ile
        35                  40                  45

Cys Cys Ser Ala Val Gln Glu Ser Ser Ala Ala Ala Val Thr Asp Lys
    50                  55                  60

Lys Glu Ala Glu Pro Ala Ala Lys Ala Ala Pro Ala Val Lys Lys
65                  70                  75                  80

Ala Pro Glu Lys Pro Lys Lys Pro Ala Lys Pro Leu Pro Gln Leu
                85                  90                  95

Met Glu Glu Asp Leu Ile Pro Ser Leu Lys Ala Thr Leu Glu Ala Gln
                100                 105                 110

Glu Asp Val Ser Gln Ile Glu Ile Ser Phe Arg Asp Asn Arg Leu Glu
            115                 120                 125

Gly Ser Phe Leu Lys Glu Asp Val Pro Tyr Ile Phe Trp Ala Phe Phe
130                 135                 140

Pro Asn Gly Asp Leu Thr Gly Pro Lys Ala Phe Ser Leu Ser Ser Tyr
145                 150                 155                 160

Gly Tyr Glu Ala Ser Thr Val Glu Pro Phe Leu Ile Asp Glu Arg Arg
                165                 170                 175

Val Thr Ala Gln Leu Val Val Phe Trp Ile Arg Lys Arg Leu Ala Ala
            180                 185                 190

Gln Gly Ile Leu Pro Val Trp Lys Glu
        195                 200

```
<210> SEQ ID NO 25
<211> LENGTH: 166
<212> TYPE: PRT
<213> ORGANISM: Trifolium subterraneum
<220> FEATURE:
<221> NAME/KEY: MISC_FEATURE
<222> LOCATION: (1)..(166)
<223> OTHER INFORMATION: DUF2996 domain-containing protein

<400> SEQUENCE: 25
```

Met Gln Ile Ala Ser Arg Phe Lys Thr Ile Ser Arg Asn Lys Ile Ile
1               5                   10                  15

Cys Ser Ala Val Gln Glu Ser Ser Thr Ser Thr Ser Ala Thr Ala Glu
            20                  25                  30

Thr Lys Glu Glu Val Lys Ala Ala Pro Lys Ala Ala Thr Glu Lys Lys
        35                  40                  45

Thr Pro Pro Ala Lys Ala Pro Val Lys Pro Leu Pro Gln Met Met Glu
    50                  55                  60

Glu Asp Val Ile Pro Ser Leu Lys Ala Ile Leu Glu Ala Gln Gln Asp
65                  70                  75                  80

Leu Ser Asp Leu Gln Leu Val Phe Gln Asp Asn Lys Leu Glu Gly Ser
                85                  90                  95

```
Phe Ser Lys Lys Gly Asn Pro Tyr Ser Phe Trp Ala Phe Phe Pro Thr
            100                 105                 110

Gly Leu Thr Gly Pro Lys Gly Phe Ser Leu Ser Ser Tyr Asn Ser Gly
        115                 120                 125

Ala Ser Thr Val Glu Pro Phe Leu Val Asp Glu Lys Lys Val Asn Ala
    130                 135                 140

Lys Leu Ile Val Phe Trp Val Glu Lys Arg Leu Ala Ala Gln Gly Ile
145                 150                 155                 160

Ile Pro Val Trp Lys Asp
                165

<210> SEQ ID NO 26
<211> LENGTH: 159
<212> TYPE: PRT
<213> ORGANISM: Populus trichocarpa
<220> FEATURE:
<221> NAME/KEY: MISC_FEATURE
<222> LOCATION: (1)..(159)
<223> OTHER INFORMATION: DUF2996 domain-containing protein

<400> SEQUENCE: 26

Met Ala Ser Lys Ser Val Ile Pro Arg Arg Arg Ile Thr Phe Ser Ala
1               5                   10                  15

Val Gln Glu Ser Ser Ala Ser Thr Val Ala Ala Asp Ala Asn Glu Val
            20                  25                  30

Lys Pro Val Glu Lys Lys Ala Pro Thr Lys Pro Lys Lys Ser Pro Ala
        35                  40                  45

Lys Pro Leu Ser Gln Leu Met Glu Glu Asp Val Ile Pro Ser Leu Lys
    50                  55                  60

Ala Thr Leu Glu Ala Gln Asp His Ile Thr Glu Leu Glu Leu Ser Phe
65                  70                  75                  80

Glu Asp Lys Arg Leu Glu Gly Ser Phe Leu Lys Lys Gly Thr Pro Tyr
                85                  90                  95

Ser Phe Trp Ala Phe Phe Pro Asp Gly Val Leu Thr Gly Pro Lys Gly
            100                 105                 110

Phe Ser Leu Ser Ser Tyr Gly Ser Gly Val Ser Thr Val Glu Pro Phe
        115                 120                 125

Leu Ile Asp Glu Lys Lys Ile Thr Glu Lys His Ile Val Phe Trp Val
    130                 135                 140

Glu Lys Arg Leu Ala Ala Gln Gly Ile Ile Pro Val Trp Arg Gly
145                 150                 155

<210> SEQ ID NO 27
<211> LENGTH: 210
<212> TYPE: PRT
<213> ORGANISM: Coffea canephora
<220> FEATURE:
<221> NAME/KEY: MISC_FEATURE
<222> LOCATION: (1)..(210)
<223> OTHER INFORMATION: DUF2996 domain-containing protein

<400> SEQUENCE: 27

Met Ala Ala Thr Ala Gly Gly Ser Ile Ala Val Ser Ser Phe Ile Ser
1               5                   10                  15

Ser Ser Asn Phe Ser Gln Lys Ala Lys Pro Thr Ser Thr Leu Ser Leu
            20                  25                  30

Ser Met Val Thr Ser Lys Ser Leu Ile Thr Ser Arg Arg Val Ala Cys
        35                  40                  45

Ser Ala Val Gln Glu Ser Ser Ala Ala Ala Ala Val Ala Ala Glu
```

```
                    50                  55                  60
Thr Lys Glu Glu Glu Glu Lys Gln Lys Glu Gly Thr Lys Glu Ala
 65                  70                  75                  80

Ala Thr Ala Lys Ala Thr Ala Pro Ala Lys Lys Pro Ala Lys
                 85                  90                  95

Ala Pro Pro Lys Pro Leu Pro Gln Leu Met Glu Glu Val Ile Pro
                100                 105                 110

Ser Leu Thr Ala Thr Leu Glu Ala Gln Glu Asp Ile Thr Gln Leu Glu
                115                 120                 125

Leu Ser Phe Gln Asp Asn Lys Leu Glu Gly Ser Phe Leu Lys Gly
130                 135                 140

Phe Pro Tyr Ser Phe Trp Ala Phe Phe Pro Asp Gly Asn Leu Thr Gly
145                 150                 155                 160

Pro Arg Gly Phe Ser Leu Ser Ser Tyr Gly Ser Gly Val Ser Thr Val
                165                 170                 175

Glu Pro Phe Leu Val Asp Glu Lys Arg Ile Thr Ala Lys His Val Val
                180                 185                 190

Phe Trp Val Arg Lys Arg Leu Ala Ala Gln Gly Ile Ile Pro Val Trp
                195                 200                 205

Lys Glu
    210

<210> SEQ ID NO 28
<211> LENGTH: 210
<212> TYPE: PRT
<213> ORGANISM: Trema orientalis
<220> FEATURE:
<221> NAME/KEY: MISC_FEATURE
<222> LOCATION: (1)..(210)
<223> OTHER INFORMATION: DUF2996 domain-containing protein

<400> SEQUENCE: 28

Met Ala Met Met Leu Arg Gly His Gly Gly Ala Ala Ala Leu Gly Leu
  1               5                  10                  15

Ser Ser Phe Pro Ser Ser Ser Ser Ser Ser Ser Tyr Leu Thr Gln
                 20                  25                  30

Asn Phe Lys Pro Thr Ser Leu Ser Ser Pro Ile Ile His Met Met Val
                 35                  40                  45

Ser Lys Ser Ile Thr Ala Arg Thr Ser Thr Ala Cys Phe Ala Val Gln
 50                  55                  60

Glu Ser Ser Thr Ser Thr Ala Val Ala Ala Asp Ala Asn Lys Glu Val
 65                  70                  75                  80

Lys Pro Ala Gln Lys Ala Ala Pro Ala Lys Pro Lys Ala Pro Val Lys
                 85                  90                  95

Ala Pro Ala Lys Ala Leu Pro Asp Met Met Glu Glu Val Ile Pro
                100                 105                 110

Ser Leu Lys Ser Val Leu Glu Ala Gln Asp Asp Val Thr Asp Ile Glu
                115                 120                 125

Leu Ser Phe Lys Glu Asn Arg Leu Glu Gly Ser Phe Ala Lys Lys Gly
130                 135                 140

Asn Pro Tyr Ser Phe Trp Ala Phe Phe Pro Ser Gly Val Leu Thr Gly
145                 150                 155                 160

Pro Lys Gly Phe Ser Leu Ser Ser Tyr Gly Leu Glu Ala Ser Thr Val
                165                 170                 175

Glu Pro Phe Leu Ile Asp Glu Arg Lys Ile Thr Ala Lys His Val Val
                180                 185                 190
```

```
Phe Trp Val Glu Lys Arg Leu Ala Ala Gln Gly Ile Ile Pro Val Trp
        195                 200                 205

Lys Asp
    210

<210> SEQ ID NO 29
<211> LENGTH: 202
<212> TYPE: PRT
<213> ORGANISM: Carica papaya
<220> FEATURE:
<221> NAME/KEY: MISC_FEATURE
<222> LOCATION: (1)..(202)
<223> OTHER INFORMATION: DUF2996 domain-containing protein

<400> SEQUENCE: 29

Met Ala Ile Leu Gly Gly Gly Ile Gly Val Ser Ser Phe Ser Tyr
1               5                   10                  15

Pro Ser Ser Gln Phe Ser Arg Lys Ala Arg Val Ala Ser Ser Ser Cys
                20                  25                  30

Phe Leu Thr Leu Ser Leu Leu Met Val Gly Lys Ser Ala Asn Lys His
            35                  40                  45

Gly Cys Asn Val Cys Ser Ala Val Gln Glu Ser Ser Ser Ala Ala
    50                  55                  60

Val Ala Thr Glu Lys Lys Glu Val Lys Glu Glu Lys Ala Ala Pro
65                  70                  75                  80

Ala Lys Pro Lys Pro Pro Ala Lys Ala Pro Val Lys Thr Leu Pro Lys
                85                  90                  95

Met Met Glu Glu Asp Ile Ile Pro Ser Leu Lys Thr Ile Leu Glu Ala
            100                 105                 110

Gln Glu Asp Ile Ser Gln Leu Glu Leu Ser Phe Gln Glu Asn Lys Leu
        115                 120                 125

Glu Gly Ser Phe Leu Lys Lys Arg Asn Pro Tyr Ser Phe Trp Ala Phe
    130                 135                 140

Phe Pro Thr Gly Thr Leu Thr Gly Pro Lys Gly Phe Ser Leu Ser Ser
145                 150                 155                 160

Tyr Gly Ser Glu Ala Ser Thr Val Glu Pro Phe Leu Val Asp Glu Lys
                165                 170                 175

Lys Ile Thr Ala Lys His Val Val Phe Trp Val Glu Lys Arg Leu Ala
            180                 185                 190

Ala Gln Gly Ile Ile Pro Val Trp Lys Asp
        195                 200

<210> SEQ ID NO 30
<211> LENGTH: 194
<212> TYPE: PRT
<213> ORGANISM: Daucus carota
<220> FEATURE:
<221> NAME/KEY: MISC_FEATURE
<222> LOCATION: (1)..(194)
<223> OTHER INFORMATION: DUF2996 domain-containing protein

<400> SEQUENCE: 30

Met Ala Thr Thr Gly Arg Ser Thr Ala Val Ala Ser Val Ser Phe Pro
1               5                   10                  15

Ser Ser Ser Cys Leu Ser Cys Lys Pro Arg Tyr Thr Ser Ser Val Ser
                20                  25                  30

Met Met Val Asn Thr Ala Val Ala Ser His Arg Ser Ile Ala Cys Ser
            35                  40                  45
```

```
Ala Val Gln Glu Ser Ser Ala Ser Ala Ser Thr Val Ser Thr
 50                  55                  60

Ala Asp Val Lys Glu Lys Pro Lys Pro Lys Ala Lys Pro Ala Lys
 65                  70                  75                  80

Ala Pro Ala Lys Pro Leu Pro Gln Met Met Glu Glu Asp Val Ile Pro
                 85                  90                  95

Pro Leu Lys Ser Ile Leu Glu Thr Gln Glu Asp Ile Ser Glu Ile Glu
                100                 105                 110

Leu Ser Phe Glu Asp Asn Arg Leu Tyr Gly Ser Phe Val Lys Lys Asn
            115                 120                 125

Ile Arg Tyr Ser Phe Trp Ala Phe Phe Pro Asp Gly Val Leu Thr Gly
        130                 135                 140

Pro Lys Gly Phe Ser Leu Ser Ser Tyr Gly Ser Glu Val Ser Thr Leu
145                 150                 155                 160

Glu Pro Phe Leu Ile Asp Glu Lys Lys Ile Thr Ala Lys His Ile Val
                165                 170                 175

Phe Trp Val Glu Lys Arg Leu Ala Ala Gln Gly Ile Ile Pro Val Trp
                180                 185                 190

Arg Glu

<210> SEQ ID NO 31
<211> LENGTH: 214
<212> TYPE: PRT
<213> ORGANISM: Juglans regia
<220> FEATURE:
<221> NAME/KEY: MISC_FEATURE
<222> LOCATION: (1)..(214)
<223> OTHER INFORMATION: DUF2996 domain-containing protein

<400> SEQUENCE: 31

Met Gln Met Thr Met Met Leu Gly Arg Ser Gly Gly Gly Gly Ala Ile
 1               5                  10                  15

Gly Val Ser Ser Phe Pro Ser Ser Ser Cys Ser Ser Ser Ser Ser
                 20                  25                  30

Ser Ser Ser Cys Phe Met Gln Asn Ala Lys Leu Thr Ser Leu Ser Thr
             35                  40                  45

Leu Pro Leu Lys Val Cys Lys Phe Val Thr His His Arg Tyr Ile Ile
 50                  55                  60

Ala Cys Ser Thr Leu Gln Glu Ser Ser Thr Ser Thr Val Thr Ala Glu
 65                  70                  75                  80

Thr Lys Glu Val Lys Thr Ala Gln Lys Lys Ala Pro Ala Lys Ala Lys
                 85                  90                  95

Pro Pro Ala Lys Ala Pro Val Lys Pro Leu Pro Gln Met Met Glu Glu
                100                 105                 110

Asp Val Ile Pro Ser Leu Lys Ala Ile Phe Glu Ala Gln Asp Asp Ile
            115                 120                 125

Ser Glu Leu Glu Leu Ser Phe His Asp Asn Arg Leu Glu Gly Ser Phe
        130                 135                 140

Leu Lys Glu Gly Asn Pro Tyr Phe Phe Trp Ala Phe Phe Pro Asn Gly
145                 150                 155                 160

Val Leu Thr Gly Pro Lys Gly Phe Ser Leu Ser Ser Tyr Gly Ser Glu
                165                 170                 175

Ala Ser Thr Val Glu Pro Phe Leu Ile Asp Glu Lys Lys Ile Thr Ala
            180                 185                 190

Asn His Val Val Phe Trp Val Glu Lys Arg Leu Ala Ala Gln Gly Ile
        195                 200                 205
```

Ile Pro Val Trp Lys Asp
    210

<210> SEQ ID NO 32
<211> LENGTH: 198
<212> TYPE: PRT
<213> ORGANISM: Macleaya cordata
<220> FEATURE:
<221> NAME/KEY: MISC_FEATURE
<222> LOCATION: (1)..(198)
<223> OTHER INFORMATION: DUF2996 domain-containing protein

<400> SEQUENCE: 32

Met Ala Ser Pro Ser Ile Asn Val Thr Cys Pro Ser Thr Lys Ser Ile
1               5                   10                  15

Lys Ile Ser Val Phe Pro Lys Leu Leu Ser Ser Val Leu Pro Thr Arg
            20                  25                  30

Asp Asn Glu Trp Lys Val His Lys Leu Ile Thr Ser Arg Gly His Val
        35                  40                  45

Val Cys Ser Ala Val Gln Glu Ser Ser Thr Ser Thr Val Thr Ala Lys
    50                  55                  60

Thr Lys Glu Ser Lys Ala Val Asp Lys Glu Ala Pro Ala Lys Pro Lys
65                  70                  75                  80

Ala Pro Ala Lys Ala Pro Ala Lys Pro Leu Pro Glu Leu Met Glu Glu
                85                  90                  95

Asp Val Ile Pro Ser Leu Lys Ala Ile Leu Glu Ala Gln Asp Asp Leu
            100                 105                 110

Ser Asp Ile Glu Leu Ser Phe Asn Asp Asn Arg Leu Glu Gly Ser Phe
        115                 120                 125

Leu Lys Asn Gly Thr Ser Tyr Ser Phe Trp Ala Phe Phe Pro Asp Gly
    130                 135                 140

Val Leu Thr Gly Pro Lys Gly Phe Ser Leu Ala Ser Tyr Gly Thr Gly
145                 150                 155                 160

Val Ser Thr Val Glu Pro Phe Leu Ile Asp Glu Lys Lys Ile Thr Ala
                165                 170                 175

Lys His Val Phe Trp Val Glu Lys Arg Leu Ala Ala Gln Gly Ile
            180                 185                 190

Leu Pro Val Trp Lys Glu
        195

<210> SEQ ID NO 33
<211> LENGTH: 208
<212> TYPE: PRT
<213> ORGANISM: Spinacia oleracea
<220> FEATURE:
<221> NAME/KEY: MISC_FEATURE
<222> LOCATION: (1)..(208)
<223> OTHER INFORMATION: DUF2996 domain-containing protein

<400> SEQUENCE: 33

Met Ala Leu Ser Pro Val Gly Val Ser Arg Ile Ser Leu Phe Lys Ala
1               5                   10                  15

Ala Ser Leu Asp Phe Asn Gly Ser Asn Arg Val Ser Ser Gly Cys Ala
            20                  25                  30

Leu Thr Pro Ser Ser Ser Asp Val Thr Arg Leu Val Val Leu Lys Ser
        35                  40                  45

Ala Ser Pro Arg Lys His Ile Ala Cys Ser Ala Val Gln Glu Ser Ser
    50                  55                  60

```
Thr Pro Thr Val Ser Ala Glu Ala Lys Glu Glu Lys Ala Ala Ala Ala
 65                  70                  75                  80

Lys Pro Ala Ala Ala Lys Pro Lys Ala Ala Lys Ala Pro Pro
                 85                  90                  95

Lys Lys Leu Pro Glu Met Met Glu Glu Asp Ile Ile Pro Ala Leu Arg
                100                 105                 110

Ser Thr Leu Glu Ala Gln Asp Asp Ile Thr Asp Leu Glu Leu Ala Phe
            115                 120                 125

Gln Asp Thr Thr Leu Glu Gly Ser Phe Met Gln Asn Gly Ile Pro Tyr
        130                 135                 140

Ser Phe Trp Ala Phe Phe Pro Asp Gly Glu Leu Thr Gly Pro Lys Gly
145                 150                 155                 160

Phe Ala Leu Ser Ser Tyr Gly Ser Glu Val Ser Thr Val Glu Pro Phe
                165                 170                 175

Leu Ile Asp Glu Lys Lys Ile Ser Ala Lys Leu Val Val Phe Trp Val
            180                 185                 190

Glu Lys Arg Leu Ala Ala Gln Gly Ile Ile Pro Val Trp Glu Lys Ile
        195                 200                 205

<210> SEQ ID NO 34
<211> LENGTH: 197
<212> TYPE: PRT
<213> ORGANISM: Olea europaea
<220> FEATURE:
<221> NAME/KEY: MISC_FEATURE
<222> LOCATION: (1)..(197)
<223> OTHER INFORMATION: DUF2996 domain-containing protein

<400> SEQUENCE: 34

Met Ala Ala Thr Ala Gly Gly Ser Ile Ala Val Ser Ser Phe Pro Ser
1               5                  10                  15

Ser Ser Phe Gly His Lys Ser Arg Pro His Ser Ser Leu Pro Arg Ala
                20                  25                  30

Ile Lys Leu Val Asn Pro Arg Gln Arg Asn Ile Ala Cys Ser Ala Val
            35                  40                  45

Gln Glu Ser Pro Thr Ser Thr Val Ala Ala Glu Thr Lys Glu Lys Lys
        50                  55                  60

Glu Lys Pro Asp Glu Ala Ala Ala Pro Ala Lys Pro Lys Pro Lys Ala
65                  70                  75                  80

Ala Ala Lys Ala Pro Ala Lys Ala Leu Pro Glu Leu Met Glu Glu Asp
                85                  90                  95

Val Ile Pro Thr Leu Glu Ala Thr Leu Gln Ala Gln Asp Asp Ile Ser
            100                 105                 110

Glu Leu Glu Leu Ser Phe Asn Asp Asn Lys Leu Glu Gly Ser Phe Leu
        115                 120                 125

Lys Lys Gly Asn Pro Tyr Ser Phe Trp Ala Phe Phe Pro Asp Gly Asn
130                 135                 140

Leu Thr Gly Pro Lys Gly Phe Ser Leu Ser Ser Tyr Gly Thr Glu Val
145                 150                 155                 160

Ser Thr Val Glu Pro Phe Leu Val Asp Glu Lys Lys Pro Thr Ala Lys
                165                 170                 175

His Val Val Phe Trp Val Glu Lys Arg Leu Ala Ala Gln Gly Ile Ile
            180                 185                 190

Pro Val Trp Asn Glu
        195
```

<210> SEQ ID NO 35
<211> LENGTH: 172
<212> TYPE: PRT
<213> ORGANISM: Amborella trichopoda
<220> FEATURE:
<221> NAME/KEY: MISC_FEATURE
<222> LOCATION: (1)..(172)
<223> OTHER INFORMATION: DUF2996 domain-containing protein

<400> SEQUENCE: 35

Met Ala Gly Gly Glu Val Leu Val Val Phe Arg Arg Gly Pro Pro Arg
1               5                   10                  15

Arg Ile Val Met Cys Ser Ala Val Gln Glu Ser Pro Thr Val Ala Ser
            20                  25                  30

Glu Thr Lys Glu Ala Val Lys Pro Glu Gly Glu Thr Pro Val Lys Glu
        35                  40                  45

Thr Pro Ala Lys Arg Ala Ala Pro Ala Lys Ala Pro Val Lys Ala Leu
    50                  55                  60

Pro Gln Phe Met Glu Glu Asp Val Ile Pro Ser Leu Arg Ala Ile Leu
65                  70                  75                  80

Glu Ala Glu Asn Asp Ile Ser Glu Ile Glu Leu Ser Phe Ser Asp Asn
                85                  90                  95

Lys Leu Glu Gly Ser Phe Val Lys Asp Gly Ile Pro Tyr Asn Phe Trp
            100                 105                 110

Ala Phe Phe Pro Ser Gly Ser Leu Val Gly Pro Lys Gly Phe Ser Leu
        115                 120                 125

Ser Ser Tyr Gly Ser Gly Ala Ser Thr Val Glu Pro Phe Leu Ile Asp
    130                 135                 140

Glu Lys Lys Ile Thr Ser Lys His Val Val Phe Trp Val Glu Lys Arg
145                 150                 155                 160

Leu Ala Ala Gln Gly Ile Leu Pro Val Trp Arg Glu
                165                 170

<210> SEQ ID NO 36
<211> LENGTH: 252
<212> TYPE: PRT
<213> ORGANISM: Gossypium raimondii
<220> FEATURE:
<221> NAME/KEY: MISC_FEATURE
<222> LOCATION: (1)..(252)
<223> OTHER INFORMATION: DUF2996 domain-containing protein

<400> SEQUENCE: 36

Met Ala Ile Val Gly Thr Arg Ala Val Gly Leu Ser Ser Phe Pro Ser
1               5                   10                  15

Ser Ser Ser Tyr Leu Ser Trp Asn Ser Arg Ala Thr Tyr Ser Ser Phe
            20                  25                  30

Ser Cys Thr Leu Asp Leu Val Tyr Met Arg Asn Met Ile Thr Ser Phe
        35                  40                  45

Ile Leu Lys Leu Thr Val Phe Leu Ile Arg Ile Arg Leu Gln Met Asp
    50                  55                  60

Val Ala Ala Ser Met Ser His Leu Ser Tyr Cys Asn Phe Asn Cys Met
65                  70                  75                  80

Ala Leu Val Gln Met Met Ser Lys Met Ile Pro Ser Arg Gly Cys Val
                85                  90                  95

Thr Cys Ser Ala Val Gln Glu Ser Ser Ser Pro Thr Lys Leu Leu Leu
            100                 105                 110

Ser Ile Ser Lys Ala His Leu Leu Lys Leu Arg Pro Pro Leu Arg Ile
        115                 120                 125

```
Arg Arg Lys Ala Ser Ala Ser Asn Gln Gln Gln Ser His Cys Arg Leu
            130                 135                 140

Pro Glu Leu Met Trp Glu Asp Val Ile Pro Pro Leu Lys Thr Ile Leu
145                 150                 155                 160

Glu Ser Gln His His Leu Ser Gln Ile Gln Leu Ser Phe Gln Asp Asn
                165                 170                 175

Lys Leu Glu Gly Ser Phe Leu Lys Asn Gly Trp Pro Tyr Ser Phe Trp
            180                 185                 190

Ala Phe Phe Pro Asn Gly Glu Leu Thr Gly Pro Lys Gly Phe Ser Leu
        195                 200                 205

Cys Ser Tyr Gly Arg Gly Ala Ser Thr Val Glu Pro Phe Leu Val Asp
    210                 215                 220

Glu Lys Lys Ile Thr Ala Lys His Val Val Phe Trp Val Glu Lys Arg
225                 230                 235                 240

Leu Ala Ala Gln Gly Ile Ile Pro Val Trp Lys Glu
                245                 250
```

<210> SEQ ID NO 37
<211> LENGTH: 210
<212> TYPE: PRT
<213> ORGANISM: Parasponia andersonii
<220> FEATURE:
<221> NAME/KEY: MISC_FEATURE
<222> LOCATION: (1)..(210)
<223> OTHER INFORMATION: DUF2996 domain-containing protein

<400> SEQUENCE: 37

```
Met Ala Met Met Leu Arg Gly His Gly Gly Ala Ala Leu Gly Leu
1               5                   10                  15

Ser Ser Phe Pro Ser Ser Ser Ser Ser Ser Ser Tyr Leu Thr Gln
            20                  25                  30

Asn Ser Lys Pro Thr Ser Leu Ser Ser Pro Ile Ile His Met Met Val
            35                  40                  45

Ser Lys Ser Ile Thr Ala Arg Thr Ser Thr Ala Tyr Phe Ala Val Gln
    50                  55                  60

Glu Ser Ser Thr Ser Thr Ala Val Ala Ala Asp Ala Ser Lys Glu Val
65                  70                  75                  80

Lys Pro Ala Gln Lys Pro Ala Pro Ala Lys Pro Lys Ala Pro Ala Lys
                85                  90                  95

Ala Pro Ala Lys Ala Leu Pro Asp Met Met Glu Glu Val Ile Pro
            100                 105                 110

Ser Leu Lys Ser Ile Leu Glu Ala Gln Asp Asp Val Thr Asp Ile Glu
        115                 120                 125

Leu Ser Phe Lys Asp Asn Arg Leu Glu Gly Ser Phe Glu Lys Lys Gly
    130                 135                 140

Asn Pro Tyr Ser Phe Trp Ala Phe Phe Pro Asn Gly Val Leu Thr Gly
145                 150                 155                 160

Pro Lys Gly Phe Ser Leu Ser Ser Tyr Gly Leu Glu Ala Ser Thr Val
                165                 170                 175

Glu Pro Phe Leu Ile Asp Glu Arg Lys Ile Thr Gly Lys His Val Val
            180                 185                 190

Phe Trp Val Glu Lys Arg Leu Ala Ala Gln Gly Ile Ile Pro Val Trp
        195                 200                 205

Lys Asp
    210
```

```
<210> SEQ ID NO 38
<211> LENGTH: 193
<212> TYPE: PRT
<213> ORGANISM: Manihot esculenta
<220> FEATURE:
<221> NAME/KEY: MISC_FEATURE
<222> LOCATION: (1)..(193)
<223> OTHER INFORMATION: DUF2996 domain-containing protein

<400> SEQUENCE: 38

Met Ala Thr Arg Gly Gly Val Met Gly Val Ser Ser Phe Pro Ser Thr
1               5                   10                  15

Pro Ser Cys Phe Cys Arg Asn Gly Arg Thr Ser Cys Ser Thr Leu Ser
            20                  25                  30

Leu Ile Ala Ser Lys Ser Ala Thr Ser Arg Arg Ser Ile Thr Cys Phe
        35                  40                  45

Ala Val Gln Glu Ser Ser Thr Ser Thr Val Glu Glu Lys Lys Val Lys
    50                  55                  60

Lys Val Ala Glu Lys Ala Ala Ala Lys Pro Lys Ala Ala Gly Lys Ala
65                  70                  75                  80

Pro Ala Lys Pro Leu Pro Gln Leu Met Glu Glu Asp Val Ile Pro Ser
                85                  90                  95

Leu Lys Ala Ile Leu Glu Ala Asp Glu Asp Ile Thr Glu Leu Glu Leu
            100                 105                 110

Ser Phe Gln Asp Asn Arg Leu Asp Gly Ser Phe Lys Lys Lys Gly Asn
        115                 120                 125

Pro Tyr Ser Phe Trp Ala Phe Phe Pro Ser Gly Asn Leu Thr Gly Pro
    130                 135                 140

Lys Gly Phe Ser Leu Ser Ser Tyr Gly Thr Glu Ala Ser Thr Val Glu
145                 150                 155                 160

Pro Phe Leu Val Asp Glu Lys Lys Ile Thr Ala Lys His Val Val Phe
                165                 170                 175

Trp Val Glu Lys Arg Leu Ala Ala Gln Gly Ile Ile Pro Val Trp Lys
            180                 185                 190

Glu

<210> SEQ ID NO 39
<211> LENGTH: 205
<212> TYPE: PRT
<213> ORGANISM: Chenopodium quinoa
<220> FEATURE:
<221> NAME/KEY: MISC_FEATURE
<222> LOCATION: (1)..(205)
<223> OTHER INFORMATION: DUF2996 domain-containing protein

<400> SEQUENCE: 39

Met Ala Leu Ala Pro Val Gly Val Ser Arg Ile Ser Leu Phe Lys Ala
1               5                   10                  15

Ala Ser Leu Asp Ile Asn Gly Ser Asn Trp Val Ser Ser Gly Cys Ala
            20                  25                  30

Leu Ala Pro Pro Ser Ala Asp Ala Thr Arg Leu Val Val Leu Lys Ser
        35                  40                  45

Ala Ala Pro Arg Lys His Ile Ala Cys Ser Ala Val Gln Glu Ser Ser
    50                  55                  60

Thr Pro Thr Val Ser Ala Glu Ser Lys Glu Glu Lys Ala Glu Ala Lys
65                  70                  75                  80

Pro Ala Ala Ala Lys Pro Lys Ala Ala Lys Ala Pro Ala Lys Lys
                85                  90                  95
```

```
Leu Pro Glu Leu Met Glu Glu Asp Val Ile Pro Asp Leu Lys Ser Ala
            100                 105                 110

Leu Glu Ala Gln Asp Asp Ile Lys Asp Leu Glu Leu Ala Phe Lys Asp
        115                 120                 125

Thr Thr Leu Glu Gly Ser Phe Gln Gln Asn Gly Ile Pro Tyr Ser Phe
    130                 135                 140

Trp Ala Phe Phe Pro Asp Gly Ala Leu Thr Gly Pro Lys Gly Phe Ala
145                 150                 155                 160

Leu Ser Ser Tyr Gly Ser Glu Val Ser Thr Val Glu Pro Phe Leu Ile
                165                 170                 175

Asp Glu Lys Lys Ile Thr Ser Lys His Val Val Phe Trp Val Leu Lys
                180                 185                 190

Arg Leu Ala Ala Gln Gly Ile Ile Pro Val Trp Glu Gln
            195                 200                 205

<210> SEQ ID NO 40
<211> LENGTH: 190
<212> TYPE: PRT
<213> ORGANISM: Gossypium hirsutum
<220> FEATURE:
<221> NAME/KEY: MISC_FEATURE
<222> LOCATION: (1)..(190)
<223> OTHER INFORMATION: DUF2996 domain-containing protein

<400> SEQUENCE: 40

Met Ala Ile Val Gly Thr Arg Ala Val Gly Leu Ser Ser Phe Pro Ser
1               5                   10                  15

Ser Ser Ser Tyr Leu Ser Trp Asn Ser Arg Ala Thr Asp Ser Ser Phe
            20                  25                  30

Ser Cys Thr Leu Ser Met Gln Met Met Ser Lys Met Ile Pro Ser Arg
        35                  40                  45

Gly Cys Val Thr Cys Ser Ala Val Gln Glu Ser Ser Ser Pro Thr Thr
    50                  55                  60

Thr Ala Glu Asn Lys Glu Glu Gly Lys Arg Pro Lys Pro Ala Ala Lys
65                  70                  75                  80

Ser Leu Pro Glu Leu Met Trp Glu Asp Val Ile Pro Pro Leu Lys Thr
                85                  90                  95

Ile Leu Glu Ser Gln His His Leu Ser Gln Ile Gln Leu Tyr Phe Gln
            100                 105                 110

Asp Asn Lys Leu Glu Gly Ser Phe Leu Lys Asn Gly Trp Pro Tyr Ser
        115                 120                 125

Phe Trp Ala Phe Phe Pro Asn Gly Glu Leu Thr Gly Pro Lys Gly Phe
    130                 135                 140

Ser Leu Cys Ser Tyr Gly Trp Gly Ala Ser Thr Val Glu Arg Phe Leu
145                 150                 155                 160

Val Asp Glu Lys Lys Ile Thr Ala Lys His Val Val Phe Trp Val Glu
                165                 170                 175

Lys Arg Leu Ala Ala Arg Gly Ile Ile Pro Val Trp Lys Glu
            180                 185                 190

<210> SEQ ID NO 41
<211> LENGTH: 193
<212> TYPE: PRT
<213> ORGANISM: Solanum tuberosum
<220> FEATURE:
<221> NAME/KEY: MISC_FEATURE
<222> LOCATION: (1)..(193)
<223> OTHER INFORMATION: DUF2996 domain-containing protein
```

<400> SEQUENCE: 41

```
Met Ala Thr Thr Gly Gly Ser Ile Ser Leu Ser Ser Phe Pro Ser Ser
1               5                   10                  15

Ser Phe Cys Arg Lys Ala Lys Pro Ile Leu Pro Ala Asp Ser Leu Glu
            20                  25                  30

Leu Arg His Leu Lys Thr Cys Lys Cys Lys Ile Ile Val Arg Asn Leu
        35                  40                  45

Val Cys Phe Ala Ala Gln Glu Ser Ser Ser Val Thr Val Ala Glu Glu
    50                  55                  60

Lys Lys Glu Ser Gln Thr Ala Glu Glu Lys Pro Lys Pro Lys Ala Lys
65                  70                  75                  80

Ala Pro Asp Lys Pro Leu Pro Gln Met Met Glu Glu Asp Val Ile Pro
                85                  90                  95

Ser Leu Lys Ala Ile Leu Glu Ser Gln Asn Asp Ile Leu Glu Leu Glu
            100                 105                 110

Leu Ser Phe Asn Asp Asn Lys Leu Glu Gly Ser Phe Leu Lys Lys Gly
        115                 120                 125

Asn Pro Tyr Ser Phe Trp Ala Phe Phe Pro Asp Gly Leu Thr Gly Pro
    130                 135                 140

Lys Gly Phe Ser Leu Ser Ser Tyr Gly Ser Gly Ala Ser Thr Val Glu
145                 150                 155                 160

Pro Phe Leu Val Asp Glu Lys Lys Ile Thr Ala Lys His Ile Val Phe
                165                 170                 175

Trp Val Glu Lys Arg Leu Ala Ala Gln Gly Ile Ile Pro Val Trp Lys
            180                 185                 190

Glu
```

<210> SEQ ID NO 42
<211> LENGTH: 197
<212> TYPE: PRT
<213> ORGANISM: Durio zibethinus
<220> FEATURE:
<221> NAME/KEY: MISC_FEATURE
<222> LOCATION: (1)..(197)
<223> OTHER INFORMATION: DUF2996 domain-containing protein

<400> SEQUENCE: 42

```
Met Leu Asn His Ser Ser Glu Thr Leu Gln Gln Ile Val Ser Lys Ser
1               5                   10                  15

Ile Ile Ser Arg Gly Cys Val Thr Cys Ser Ala Val Gln Glu Ser Ser
            20                  25                  30

Ser Pro Thr Ala Thr Ala Lys Thr Lys Glu Ala Thr Pro Ala Glu Ala
        35                  40                  45

Lys Pro Ser Ala Ile Ala Glu Thr Lys Ala Ala Ala Ala Ala Glu Lys
    50                  55                  60

Glu Glu Val Lys Ala Ala Pro Lys Ala Ala Ala Arg Pro Lys Pro
65                  70                  75                  80

Ala Ala Lys Thr Pro Ala Lys Pro Leu Pro Glu Leu Met Val Glu Asp
                85                  90                  95

Val Ile Pro Ser Leu Lys Thr Ile Leu Glu Gly Gln Asp Asp Leu Ser
            100                 105                 110

Glu Ile Glu Leu Ser Phe Gln Asp Asn Lys Leu Glu Gly Ser Phe Leu
        115                 120                 125

Lys Lys Gly Cys Pro Tyr Ser Phe Trp Ala Phe Phe Pro Ser Gly Asp
    130                 135                 140
```

Leu Ser Gly Pro Lys Gly Phe Ser Leu Ser Ser Tyr Gly Ser Gly Ala
145                 150                 155                 160

Ser Thr Val Glu Pro Phe Leu Val Asp Glu Lys Lys Ile Thr Ala Lys
                165                 170                 175

His Val Val Phe Trp Val Glu Lys Arg Leu Ala Ala Gln Gly Ile Ile
            180                 185                 190

Pro Val Trp Lys Glu
        195

<210> SEQ ID NO 43
<211> LENGTH: 213
<212> TYPE: PRT
<213> ORGANISM: Glycine max
<220> FEATURE:
<221> NAME/KEY: MISC_FEATURE
<222> LOCATION: (1)..(213)
<223> OTHER INFORMATION: DUF2996 domain-containing protein

<400> SEQUENCE: 43

Met Gln Met Ala Ile Leu Leu Arg Gly Gly Ala Leu Gly Asp Ser Ser
1               5                   10                  15

Phe Arg Leu Cys Ser Leu Thr Ser Thr Ser Ser Leu His Val Ser Gln
            20                  25                  30

Asn Val Ala Ile Pro Thr Ser Ser Ser Pro Ile Leu Pro Leu Ile
            35                  40                  45

Ala Ser Lys Phe Lys Thr Ala Ser Arg Asn Arg Ile Thr Cys Ser Ala
        50                  55                  60

Val Gln Glu Ser Ser Pro Ser Thr Ala Ala Thr Ala Glu Thr Lys
65                  70                  75                  80

Glu Glu Val Lys Glu Ala Pro Lys Ala Ala Pro Ala Lys Lys Pro
                85                  90                  95

Pro Ala Lys Ala Pro Ala Lys Pro Leu Pro Gln Met Met Glu Glu Asp
            100                 105                 110

Val Ile Pro Ser Leu Lys Ala Ile Phe Glu Ala Gln Glu Asp Phe Ser
        115                 120                 125

Asn Ile Glu Leu Val Phe Lys Asp Asn Lys Leu Glu Gly Ser Phe Leu
    130                 135                 140

Lys Lys Gly Asn Pro Tyr Ser Phe Trp Ala Phe Phe Pro Thr Gly Asn
145                 150                 155                 160

Leu Ile Gly Pro Lys Gly Phe Ser Leu Ser Ser Tyr Asn Ser Arg Ala
                165                 170                 175

Ser Thr Val Glu Pro Phe Leu Val Asp Glu Lys Lys Ile Thr Ala Arg
            180                 185                 190

His Ile Ile Phe Trp Val Glu Lys Arg Leu Ala Ala Gln Gly Ile Ile
        195                 200                 205

Pro Val Trp Lys Asp
    210

<210> SEQ ID NO 44
<211> LENGTH: 210
<212> TYPE: PRT
<213> ORGANISM: Punica granatum
<220> FEATURE:
<221> NAME/KEY: MISC_FEATURE
<222> LOCATION: (1)..(210)
<223> OTHER INFORMATION: DUF2996 domain-containing protein

<400> SEQUENCE: 44

```
Met Ala Ile Leu Gly Gly Gln Ala Val Gly Val Pro Ser Phe Leu Ser
1               5                   10                  15

Ser Ser Ser Tyr His Ala Ser Gln Ser Asn Lys Ile Thr Gln Ser Pro
            20                  25                  30

Ser Thr Leu Ser Thr Val Gly Ser Arg Leu Gly Ala Ser Arg Arg Ile
        35                  40                  45

Val Ala Cys Ser Ala Val Gln Glu Ser Ser Ala Ala Ala Thr Pro Thr
50                  55                  60

Thr Thr Val Ala Thr Ser Glu Thr Ala Ser Ala Glu Thr Lys Glu Ala
65                  70                  75                  80

Lys Ala Ala Pro Lys Glu Ala Ala Lys Pro Lys Arg Pro Ala Lys
                85                  90                  95

Ala Pro Val Lys Pro Leu Pro Leu Met Glu Glu Val Ile Pro
                100                 105                 110

Gln Leu Lys Glu Ile Leu Gln Ala Gln Glu Asp Leu Ser Glu Ile Glu
            115                 120                 125

Leu Thr Phe Gln Asp Asn Arg Leu Glu Gly Ser Phe Leu Lys Lys Gly
        130                 135                 140

Asn Pro His Ser Phe Trp Ala Phe Phe Pro Asn Gly Asp Leu Thr Gly
145                 150                 155                 160

Pro Lys Gly Phe Ser Leu Ser Ser Tyr Gly Ser Gly Ala Ser Thr Val
                165                 170                 175

Glu Pro Phe Leu Val Asp Glu Lys Lys Ile Thr Ala Asn Leu Val Ile
            180                 185                 190

Phe Trp Val Glu Lys Arg Leu Ala Ala Gln Gly Ile Ile Pro Val Trp
        195                 200                 205

Lys Glu
    210

<210> SEQ ID NO 45
<211> LENGTH: 218
<212> TYPE: PRT
<213> ORGANISM: Fragaria vesca
<220> FEATURE:
<221> NAME/KEY: MISC_FEATURE
<222> LOCATION: (1)..(218)
<223> OTHER INFORMATION: DUF2996 domain-containing protein

<400> SEQUENCE: 45

Met Ala Ser Ala Asn Ile Leu Ser Met Ala Lys Pro Ser Pro Gln Glu
1               5                   10                  15

Asn Gly Lys Gly Phe Val Glu Ser Ser Thr Leu Arg Asn Thr Ser
            20                  25                  30

Ala Asn Cys Leu Gln Phe Gly Arg Lys Asn Ser Asp Asp Ser Val Ser
        35                  40                  45

Val Val Ala Phe His Ser Ser Pro Ala Gln Gln Met Val Ser Lys Ala
50                  55                  60

Val Ala Ser Lys Arg Thr Ile Ala Cys Ser Ala Leu Gln Glu Ser Ser
65                  70                  75                  80

Thr Ser Thr Val Ala Ala Glu Thr Lys Glu Val Lys Ala Ala Pro Ala
                85                  90                  95

Lys Pro Lys Ala Pro Ala Lys Ala Pro Val Lys Pro Leu Pro Gln Met
                100                 105                 110

Met Glu Glu Asp Ile Ile Pro Ser Leu Lys Ala Ile Leu Glu Thr Pro
            115                 120                 125

Gln Asn Gln Leu Ser Asp Ile Glu Leu Phe Phe Glu Asp Asn Lys Leu
```

```
                130                 135                 140
Glu Gly Ser Phe Leu Lys Lys Gly Asn Ser Tyr Ser Phe Trp Ala Phe
145                 150                 155                 160

Phe Pro Asn Gly Asp Leu Thr Gly Pro Lys Gly Phe Ser Leu Ser Ser
                165                 170                 175

Tyr Gly Leu Gly Ala Ser Thr Val Glu Pro Phe Leu Val Asp Glu Lys
            180                 185                 190

Lys Ile Thr Ala Arg His Ile Ile Phe Trp Val Glu Lys Arg Leu Ala
        195                 200                 205

Ala Gln Gly Ile Ile Pro Val Trp Lys Asp
    210                 215
```

<210> SEQ ID NO 46
<211> LENGTH: 205
<212> TYPE: PRT
<213> ORGANISM: Beta vulgaris
<220> FEATURE:
<221> NAME/KEY: MISC_FEATURE
<222> LOCATION: (1)..(205)
<223> OTHER INFORMATION: DUF2996 domain-containing protein

<400> SEQUENCE: 46

```
Met Ala Leu Ser Pro Val Gly Val Ser Arg Ile Ser Leu Phe Lys Ala
1               5                   10                  15

Ala Ser Leu Asp Phe Asn Gly Ser Asn Trp Val Ser Ser Ser Arg Ala
            20                  25                  30

Leu Ala Pro Pro Ser Ser Asp Pro Thr Arg Leu Val Val Leu Lys Ser
        35                  40                  45

Ala Ala Pro Cys Lys His Ile Ala Cys Ser Ala Val Gln Glu Ser Ser
    50                  55                  60

Thr Pro Thr Val Ser Ala Asp Ala Lys Glu Lys Ala Glu Ala Ile
65                  70                  75                  80

Pro Ala Ala Ala Lys Pro Lys Pro Ala Ala Lys Ala Pro Ala Lys Ala
                85                  90                  95

Leu Pro Gln Met Met Glu Glu Asp Val Ile Pro Ala Leu Lys Ser Ile
            100                 105                 110

Leu Glu Ala Gln Asp Asp Ile Thr Asp Leu Glu Leu Ala Phe Lys Asp
        115                 120                 125

Asn Thr Leu Glu Gly Ser Phe Leu Gln Lys Asp Lys Ala Tyr Ser Phe
    130                 135                 140

Trp Ala Phe Phe Pro Asp Gly Asn Leu Thr Gly Pro Lys Gly Phe Ser
145                 150                 155                 160

Leu Cys Ser Tyr Gly Ser Glu Val Ser Thr Val Glu Pro Phe Leu Ile
                165                 170                 175

Asp Glu Lys Lys Ile Thr Pro Arg His Val Val Phe Trp Val Glu Lys
            180                 185                 190

Arg Leu Ala Ala Gln Gly Ile Ile Pro Val Trp Glu Arg
        195                 200                 205
```

<210> SEQ ID NO 47
<211> LENGTH: 199
<212> TYPE: PRT
<213> ORGANISM: Citrus clementina
<220> FEATURE:
<221> NAME/KEY: MISC_FEATURE
<222> LOCATION: (1)..(199)
<223> OTHER INFORMATION: DUF2996 domain-containing protein

<400> SEQUENCE: 47

```
Met Ser Ile Leu Gly Gly Arg Ala Val Gly Val Ser Ser Phe Pro Ser
1               5                   10                  15

Ser Ser Tyr Phe Ser Arg Asn Val Lys Ser Thr Ser Ser Ala Phe Pro
            20                  25                  30

Leu Gln Met Ala Cys Thr Ser Ala Ala Leu Arg Gly Cys Ile Ala Cys
        35                  40                  45

Ser Ala Val Gln Glu Thr Ser Thr Ser Ala Val Ala Ala Glu Thr Lys
50                  55                  60

Glu Ala Lys Pro Val Glu Lys Glu Ala Pro Thr Lys Pro Lys Pro Pro
65                  70                  75                  80

Ala Arg Ala Pro Lys Ala Pro Ala Lys Pro Leu Pro Glu Leu Met Glu
                85                  90                  95

Glu Asp Val Ile Pro Ser Leu Lys Ala Ile Leu Glu Ala Gln Asp Asp
            100                 105                 110

Leu Ser Asn Ile Glu Leu Cys Phe Lys Asp Asn Lys Leu Glu Gly Ser
        115                 120                 125

Phe Met Lys Lys Gly Asn Asn Tyr Ser Phe Trp Ala Phe Phe Pro Asn
130                 135                 140

Gly Ile Leu Ala Gly Pro Lys Gly Phe Ser Leu Ser Ser Tyr Gly Ser
145                 150                 155                 160

Gly Ala Ser Thr Val Glu Pro Phe Leu Ile Asp Glu Lys Lys Ile Thr
                165                 170                 175

Ala Arg His Val Val Phe Trp Val Glu Lys Arg Leu Ala Ala Gln Gly
            180                 185                 190

Ile Leu Pro Val Trp Lys Glu
        195

<210> SEQ ID NO 48
<211> LENGTH: 187
<212> TYPE: PRT
<213> ORGANISM: Erythranthe guttata
<220> FEATURE:
<221> NAME/KEY: MISC_FEATURE
<222> LOCATION: (1)..(187)
<223> OTHER INFORMATION: DUF2996 domain-containing protein

<400> SEQUENCE: 48

Met Ala Thr Gly Gly Ser Val Ala Val Phe Ser Cys Pro Ser Ser Tyr
1               5                   10                  15

Phe Cys Gln Lys Ala Arg Pro Ser Thr Pro Ser Ser Leu Ser Leu Val
            20                  25                  30

Phe Asn Val Ala Asn Lys Arg His Lys Thr Cys Cys Leu Ala Val Gln
        35                  40                  45

Glu Ser Ser Thr Ser Thr Glu Val Lys Lys Ala Asp Glu Glu Thr Ala
50                  55                  60

Ala Ala Lys Pro Lys Ala Ala Ala Lys Ala Pro Met Lys Pro Leu Pro
65                  70                  75                  80

Glu Leu Met Ala Asp Glu Ile Ile Pro Pro Leu Lys Ser Ile Leu Glu
                85                  90                  95

Ala Gln Gln Asp Leu Ser Cys Leu Glu Leu Ser Phe Asn Glu Asn Gln
            100                 105                 110

Leu Glu Gly Ser Phe Met Lys Lys Gly Ile Pro Tyr Ser Phe Trp Ala
        115                 120                 125

Phe Phe Pro Asp Gly Thr Ile Thr Gly Ala Lys Gly Phe Ser Ile Ser
130                 135                 140
```

Ser Tyr Gly Thr Gly Val Ser Thr Val Glu Pro Phe Leu Val Asp Glu
145                 150                 155                 160

Lys Lys Pro Thr Ala Lys Phe Val Val Phe Trp Ile Glu Lys Arg Leu
                165                 170                 175

Ala Ala Gln Gly Ile Ile Pro Val Trp Thr Asp
            180                 185

<210> SEQ ID NO 49
<211> LENGTH: 197
<212> TYPE: PRT
<213> ORGANISM: Nelumbo nucifera
<220> FEATURE:
<221> NAME/KEY: MISC_FEATURE
<222> LOCATION: (1)..(197)
<223> OTHER INFORMATION: DUF2996 domain-containing protein

<400> SEQUENCE: 49

Met Ala Ala Pro Pro Ile Asn Leu Asn Cys Pro Leu Thr Lys Pro Ile
1               5                   10                  15

Lys Val Ser Val Tyr Pro Pro Leu Ser Ser Val Leu Pro Thr Lys His
                20                  25                  30

Glu Gln Arg Lys Val Gly Asn Leu Val Ile Ser Arg Gly Asn Phe Phe
            35                  40                  45

Cys Ser Ala Val Gln Glu Ser Ser Thr Ser Thr Val Ala Ala Asp Lys
50                  55                  60

Pro Glu Ala Lys Thr Ala Ala Lys Glu Ala Pro Ala Lys Pro Lys Pro
65                  70                  75                  80

Pro Ala Lys Ala Pro Ala Lys Pro Leu Pro Gln Leu Met Glu Glu Asp
                85                  90                  95

Val Ile Pro Ala Leu Lys Thr Ile Leu Glu Ala Gln Asp Asp Leu Ser
            100                 105                 110

Glu Ile Glu Leu Phe Phe Arg Asp Asn Lys Leu Glu Gly Ser Phe Leu
        115                 120                 125

Lys Asn Gly Phe Pro Tyr Ser Phe Trp Ala Phe Pro Asn Gly Val
130                 135                 140

Leu Thr Gly Pro Lys Gly Phe Ser Leu Ser Ser Tyr Gly Ser Gly Val
145                 150                 155                 160

Ser Thr Val Glu Pro Phe Leu Ile Asp Glu Lys Arg Ile Thr Ala Lys
                165                 170                 175

His Val Val Phe Trp Val Glu Lys Arg Leu Ala Ala Gln Gly Ile Ile
            180                 185                 190

Pro Val Trp Lys Glu
        195

<210> SEQ ID NO 50
<211> LENGTH: 193
<212> TYPE: PRT
<213> ORGANISM: Momordica charantia
<220> FEATURE:
<221> NAME/KEY: MISC_FEATURE
<222> LOCATION: (1)..(193)
<223> OTHER INFORMATION: DUF2996 domain-containing protein

<400> SEQUENCE: 50

Met Ala Met Ile Leu Lys Gly Gly Gly Gly Ile Gly Val Pro Thr Ala
1               5                   10                  15

Thr Cys Phe Ser Gln Ile Ser Lys Pro Ser Pro Ile Phe Ser Ile His
                20                  25                  30

Thr Ile Tyr Lys Leu Ala Ala Glu Arg Lys Val Ile Cys Cys Ser Thr

```
                35                  40                  45
Leu Gln Glu Ser Ser Thr Pro Thr Val Ala Ala Glu Pro Lys Glu Met
 50                  55                  60

Lys Val Val Glu Lys Glu Ala Pro Ala Lys Thr Lys Pro Pro Ala Lys
 65                  70                  75                  80

Ala Pro Val Lys Ala Leu Pro Glu Leu Met Glu Glu Asp Val Ile Pro
                 85                  90                  95

Ser Leu Lys Ala Ile Leu Glu Ala Gln Ala Asp Val Ser Asp Ile Glu
                100                 105                 110

Leu Ser Phe Gln Asp Asp Arg Leu Asp Gly Ser Phe Leu Lys Asn Gly
            115                 120                 125

Val Pro Tyr Ser Phe Trp Ala Phe Phe Pro Asn Gly Leu Thr Gly Pro
130                 135                 140

Lys Gly Phe Ser Leu Ser Ser Tyr Gly Tyr Gly Ser Ser Val Glu
145                 150                 155                 160

Pro Phe Leu Val Asp Glu Lys Lys Ile Thr Ala Lys His Val Val Phe
                165                 170                 175

Trp Ile Glu Lys Arg Leu Ala Ala Gln Gly Ile Ile Pro Val Trp Lys
            180                 185                 190

Asp

<210> SEQ ID NO 51
<211> LENGTH: 200
<212> TYPE: PRT
<213> ORGANISM: Elaeis guineensis
<220> FEATURE:
<221> NAME/KEY: MISC_FEATURE
<222> LOCATION: (1)..(200)
<223> OTHER INFORMATION: DUF2996 domain-containing protein

<400> SEQUENCE: 51

Met Ala Ser Gln Ser Leu Asn Val Tyr Ser Pro Leu Thr Arg Gln Val
  1               5                  10                  15

Lys Gly Asp Ile Val Pro Val Phe Ser Lys Ala Leu Val Thr Gly Asp
                 20                  25                  30

Arg Arg Gln Lys His Gly Arg Val Ile Leu Ser Leu Gly Arg Val Ile
             35                  40                  45

Cys Ser Ala Val Gln Glu Ser Ser Ala Ala Val Thr Asp Lys Lys
 50                  55                  60

Glu Ala Glu Pro Ala Ala Lys Ala Pro Ala Pro Ala Val Lys Lys Ala
 65                  70                  75                  80

Pro Glu Lys Pro Lys Lys Pro Leu Pro Lys Pro Leu Gln Leu Met
                 85                  90                  95

Glu Glu Asp Leu Ile Pro Ser Leu Lys Ala Thr Leu Glu Ala Gln Glu
                100                 105                 110

Asp Val Ser Gln Ile Glu Leu Ser Phe Arg Asp Asn Arg Leu Glu Gly
            115                 120                 125

Ser Phe Leu Gln Lys Asp Ile Pro Tyr Asn Phe Trp Ala Phe Phe Pro
130                 135                 140

Asn Gly Glu Leu Thr Gly Pro Lys Ala Phe Ser Leu Ser Ser Tyr Gly
145                 150                 155                 160

Tyr Glu Ala Ser Thr Val Glu Pro Phe Leu Ile Asp Glu Arg Arg Val
                165                 170                 175

Ser Ala Gln Leu Val Val Phe Trp Ile Arg Lys Arg Leu Ala Ala Gln
            180                 185                 190
```

```
Gly Ile Leu Pro Val Trp Glu Glu
        195                 200
```

<210> SEQ ID NO 52
<211> LENGTH: 256
<212> TYPE: PRT
<213> ORGANISM: Malus domestica
<220> FEATURE:
<221> NAME/KEY: MISC_FEATURE
<222> LOCATION: (1)..(256)
<223> OTHER INFORMATION: DUF2996 domain-containing protein

<400> SEQUENCE: 52

```
Met Ile Gly Gln Glu Lys Arg Arg Trp Phe Tyr Phe Ser Gly Glu Leu
1               5                   10                  15

Ser Ser Lys Leu Ile Thr Lys Gln Ala Ser Met Ala Ser Ala Ile Leu
            20                  25                  30

Ser Leu Pro Lys Pro Ser Pro Leu Gln Val Gln Leu His Ala Phe Gln
        35                  40                  45

Cys Xaa Arg Arg Xaa Gln Pro Asn Gly Lys His Leu Ala Glu Phe Ser
    50                  55                  60

Ala Leu Pro Lys Pro Ser Ala Arg Leu Pro Phe Arg Arg Lys Thr Ser
65                  70                  75                  80

Asn His Glu Met Xaa Lys Ser Lys Val Val Ala Ser Gln Arg Lys Arg
                85                  90                  95

Asn Ile Ala Trp Ser Ala Leu Gln Glu Ser Ser Thr Ser Thr Ala Asp
            100                 105                 110

Ala Asp Ala Ala Asp Pro Ser Thr Lys Glu Val Lys Thr Ala Asp Gln
        115                 120                 125

Lys Ala Ala Ala Pro Ala Lys Pro Lys Val Ala Ala Lys Ala Pro Val
    130                 135                 140

Lys Ala Leu Pro Gln Met Met Glu Glu Asp Val Ile Pro Pro Leu Lys
145                 150                 155                 160

Ala Ile Leu Gln Thr Gln Asp Glu Leu Ser Asn Ile Glu Leu Cys Phe
                165                 170                 175

Gln Asp Asn Arg Leu Glu Gly Ser Phe Ile Lys Lys Gly Asn Pro Tyr
            180                 185                 190

Ser Phe Trp Val Phe Phe Pro Ser Gly Val Leu Xaa Gly Pro Lys Gly
        195                 200                 205

Phe Ser Leu Ser Ser Tyr Gly Ser Glu Ala Ser Thr Val Glu Pro Phe
    210                 215                 220

Leu Val Asp Glu Lys Lys Ile Thr Ala Lys His Ile Val Phe Trp Val
225                 230                 235                 240

Glu Lys Arg Leu Ala Ala Gln Gly Ile Ile Pro Val Trp Lys Leu Asp
                245                 250                 255
```

<210> SEQ ID NO 53
<211> LENGTH: 185
<212> TYPE: PRT
<213> ORGANISM: Quercus suber
<220> FEATURE:
<221> NAME/KEY: MISC_FEATURE
<222> LOCATION: (1)..(185)
<223> OTHER INFORMATION: DUF2996 domain-containing protein

<400> SEQUENCE: 53

```
Met Gly Asp Gln Lys Gln Asp Asp Gly Leu Ser Thr Lys Pro Thr Ser
1               5                   10                  15

Leu Ser Thr Leu Ser Pro Arg Val Cys Lys Leu Val Thr Asn His Arg
```

```
            20                  25                  30
Asn Met Val Ala Trp Ser Ala Val Gln Glu Ser Ser Thr Ser Thr Val
            35                  40                  45
Ala Ala Glu Lys Lys Glu Val Lys Thr Ala Gln Asp Glu Ala Pro Ala
        50                  55                  60
Lys Ala Lys Pro Pro Ala Lys Ala Pro Ala Lys Pro Leu Pro Gln Leu
 65                  70                  75                  80
Met Glu Glu Asp Val Ile Pro Ser Leu Lys Ala Ile Leu Glu Ala Gln
                    85                  90                  95
Pro Asp Leu Ser Glu Ile Glu Leu Ser Phe Gln Asp Asn Arg Leu Glu
                100                 105                 110
Gly Ser Phe Leu Lys Lys Asp Asn Pro Tyr Ser Phe Trp Ala Phe Phe
                115                 120                 125
Pro Asp Gly Val Leu Thr Gly Ala Lys Gly Phe Ser Leu Ser Ser Tyr
            130                 135                 140
Gly Ser Glu Ala Ser Thr Val Glu Pro Phe Leu Ile Asp Glu Lys Lys
145                 150                 155                 160
Ile Thr Gly Lys His Val Val Phe Trp Val Glu Lys Arg Leu Ala Ala
                    165                 170                 175
Gln Gly Ile Ile Pro Val Trp Lys Asp
                180                 185
```

<210> SEQ ID NO 54
<211> LENGTH: 196
<212> TYPE: PRT
<213> ORGANISM: Apostasia odorata
<220> FEATURE:
<221> NAME/KEY: MISC_FEATURE
<222> LOCATION: (1)..(196)
<223> OTHER INFORMATION: DUF2996 domain-containing protein

<400> SEQUENCE: 54

```
Met Ala Ser Arg Ser Ile Asn Ile His Ser Pro Leu Pro Arg Pro Pro
 1               5                  10                  15
Lys Thr Phe Ser Ser Gln Asn Pro Gln Ile Ser Ser Cys Arg Phe Asp
                20                  25                  30
Ser Ala Lys Asn Thr Ile Ser Gly Ser Arg Met Ile Val Cys Ser Ala
            35                  40                  45
Leu Gln Glu Ser Ser Thr Ala Thr Val Ser Asp Lys Lys Glu Glu Ala
        50                  55                  60
Ala Ala Lys Ala Ala Pro Leu Pro Ala Lys Glu Ala Pro Pro Lys Pro
 65                  70                  75                  80
Lys Lys Ala Pro Ala Lys Pro Leu Pro Glu Met Met Glu Glu Asp Val
                    85                  90                  95
Ile Pro Ser Leu Arg Ala Ala Leu Glu Ala Gln Gly Glu Leu Ser Gln
                100                 105                 110
Ile Asp Leu Ser Phe Lys Asn Asn Thr Leu Glu Gly Ser Phe Leu Lys
                115                 120                 125
Lys Asp Lys Pro Tyr Tyr Phe Trp Val Phe Phe Leu Asn Gly Asp Leu
            130                 135                 140
Thr Gly Pro Lys Gly Phe Ser Leu Ser Ser Tyr Gly Ser Gly Val Ser
145                 150                 155                 160
Thr Val Glu Pro Phe Leu Val Asp Glu Lys Arg Ile Thr Ala Lys Leu
                    165                 170                 175
Val Val Phe Trp Val Arg Lys Arg Leu Ala Ala Gln Gly Ile Phe Pro
                180                 185                 190
```

```
Val Trp Glu Asp
        195
```

<210> SEQ ID NO 55
<211> LENGTH: 201
<212> TYPE: PRT
<213> ORGANISM: Aquilegia coerulea
<220> FEATURE:
<221> NAME/KEY: MISC_FEATURE
<222> LOCATION: (1)..(201)
<223> OTHER INFORMATION: DUF2996 domain-containing protein

<400> SEQUENCE: 55

```
Met Pro Tyr Asn Met Ala Cys Arg Ser Val Asn Leu Pro Ser Pro Leu
1               5                   10                  15

Met Lys Ser Ile Arg Val Ser Ser Phe Pro Val Phe Ser Thr Ile Leu
            20                  25                  30

Pro Ala Lys Asp Glu Gln Lys Ala Cys Met Leu Ala Leu Ser Val Arg
        35                  40                  45

Thr Val Lys Cys Ser Ala Val Gln Glu Thr Ser Thr Ser Thr Ala Ser
    50                  55                  60

Ala Glu Thr Lys Glu Thr Asn Val Val Lys Lys Ala Ala Pro Ala Pro
65                  70                  75                  80

Lys Pro Lys Val Pro Ala Lys Ala Pro Ala Lys Pro Leu Pro Gln Leu
                85                  90                  95

Met Glu Glu Asp Val Val Pro Ser Leu Lys Ala Thr Phe Glu Ala Gln
            100                 105                 110

Asp Asp Leu Ser Glu Ile Glu Val Phe Phe Gln Asp Asn Arg Leu Glu
        115                 120                 125

Gly Ser Phe Met Lys Asn Ala Thr Arg Tyr Thr Phe Trp Ala Phe Phe
    130                 135                 140

Pro Asp Gly Val Leu Thr Gly Pro Lys Gly Phe Ser Leu Ser Ser Tyr
145                 150                 155                 160

Gly Ser Glu Val Ser Thr Val Glu Pro Phe Leu Ile Asp Glu Lys Lys
                165                 170                 175

Ile Thr Gly Lys Met Ile Val Phe Trp Ile Glu Lys Arg Leu Ala Ala
            180                 185                 190

Gln Gly Ile Leu Pro Val Trp Lys Asp
        195                 200
```

<210> SEQ ID NO 56
<211> LENGTH: 199
<212> TYPE: PRT
<213> ORGANISM: Citrus sinensis
<220> FEATURE:
<221> NAME/KEY: MISC_FEATURE
<222> LOCATION: (1)..(199)
<223> OTHER INFORMATION: DUF2996 domain-containing protein

<400> SEQUENCE: 56

```
Met Ser Ile Leu Gly Gly Arg Ala Val Gly Val Ser Ser Phe Pro Ser
1               5                   10                  15

Ser Ser Tyr Phe Ser Arg Asn Val Lys Ser Thr Ser Ser Ala Phe Pro
            20                  25                  30

Leu Gln Met Ala Cys Thr Ser Ala Ala Leu Arg Gly Cys Ile Ala Cys
        35                  40                  45

Ser Ala Val Gln Glu Thr Ser Thr Ser Ala Val Ala Ala Glu Thr Lys
    50                  55                  60
```

```
Glu Ala Lys Pro Val Glu Lys Glu Ala Pro Lys Pro Lys Pro Pro
65                  70                  75                  80

Ala Arg Ala Pro Lys Ala Pro Ala Lys Pro Leu Pro Glu Leu Met Glu
                85                  90                  95

Glu Asp Val Ile Pro Ser Leu Lys Ala Ile Leu Glu Ala Gln Asp Asp
            100                 105                 110

Leu Ser Asn Ile Glu Leu Cys Phe Lys Asp Asn Lys Leu Glu Gly Ser
            115                 120                 125

Phe Met Lys Lys Gly Asn Asn Tyr Ser Phe Trp Ala Phe Phe Pro Asn
130                 135                 140

Gly Ile Leu Ala Gly Pro Lys Gly Phe Ser Leu Ser Ser Tyr Gly Ser
145                 150                 155                 160

Gly Ala Ser Thr Val Glu Pro Phe Leu Ile Asp Glu Lys Lys Ile Thr
                165                 170                 175

Ala Arg His Val Val Phe Trp Val Glu Lys Arg Leu Ala Ala Gln Gly
            180                 185                 190

Ile Leu Pro Val Trp Lys Glu
            195
```

```
<210> SEQ ID NO 57
<211> LENGTH: 211
<212> TYPE: PRT
<213> ORGANISM: Cicer arietinum
<220> FEATURE:
<221> NAME/KEY: MISC_FEATURE
<222> LOCATION: (1)..(211)
<223> OTHER INFORMATION: DUF2996 domain-containing protein

<400> SEQUENCE: 57

Met Gln Met Ala Leu Leu Leu Arg Gly Gly Thr Leu Gly Asp Ser Ser
1               5                   10                  15

Phe Arg Leu Cys Ser Leu Thr Ser Ser Ser Ala Ser His Val Ser
                20                  25                  30

Gln Asn Val Val Ile Pro Thr Ser Ser Ser Pro Ile Leu Pro Leu
            35                  40                  45

Ile Ala Ser Arg Phe Lys Thr Phe Ser Arg Asn Lys Ile Thr Cys Ser
50                  55                  60

Ala Val Gln Glu Ser Ser Thr Ser Thr Ser Ala Glu Thr Lys
65                  70                  75                  80

Glu Glu Val Lys Thr Val Pro Lys Ala Ala Thr Glu Lys Lys Ala Pro
                85                  90                  95

Ala Lys Ala Pro Val Lys Pro Leu Pro Gln Met Met Glu Glu Asp Val
            100                 105                 110

Ile Pro Ser Leu Lys Thr Ile Leu Glu Ala Gln Gln Asp Leu Ser Asp
            115                 120                 125

Ile Asp Leu Val Phe Gln Asp Asn Lys Leu Glu Gly Ser Phe Leu Lys
130                 135                 140

Lys Gly Asn Pro Tyr Ser Phe Trp Ala Phe Phe Pro Thr Gly Ile Thr
145                 150                 155                 160

Gly Pro Lys Gly Phe Ala Leu Ser Ser Tyr Asn Ser Gly Ala Ser Thr
                165                 170                 175

Val Glu Pro Phe Leu Ile Asp Glu Lys Lys Ile Thr Ser Lys His Ile
            180                 185                 190

Val Phe Trp Val Glu Lys Arg Leu Ala Ala Gln Gly Ile Ile Pro Val
            195                 200                 205

Trp Lys Asp
```

-continued

```
<210> SEQ ID NO 58
<211> LENGTH: 234
<212> TYPE: PRT
<213> ORGANISM: Prunus avium
<220> FEATURE:
<221> NAME/KEY: MISC_FEATURE
<222> LOCATION: (1)..(234)
<223> OTHER INFORMATION: DUF2996 domain-containing protein

<400> SEQUENCE: 58

Met Ala Ala Ile Ser Ser Val Val Gly Thr Gly Ser Val Pro Gln Ile
1               5                   10                  15

Gln Asn Arg Ser Gly Leu Ala Pro Phe Thr Pro Leu His Ile Ser Leu
            20                  25                  30

Leu Ser Pro Thr Arg Arg Leu Leu Glu Val Gly Ala Cys Arg Thr Ser
        35                  40                  45

Thr Pro Ser Ala Ile Asp Asp Arg Thr Ser Phe Cys Leu Ser Lys Pro
    50                  55                  60

Lys Phe Asp Asn Ala Gly Gln His Thr Val Ser Lys Leu Val Thr Ser
65                  70                  75                  80

Gln Arg Asn Ile Val Cys Ser Ala Leu Pro Glu Ser Ser Thr Ser Thr
                85                  90                  95

Val Ala Ala Asp Thr Lys Glu Val Lys Thr Ala Gln Lys Ala Ala Pro
            100                 105                 110

Ala Lys Pro Lys Val Ala Ala Lys Ala Pro Val Lys Pro Leu Pro Gln
        115                 120                 125

Met Met Glu Glu Asp Val Ile Pro Gln Leu Lys Ala Ile Leu Glu Thr
    130                 135                 140

Gln Asp Glu Leu Ser Asp Ile Glu Leu Ser Phe Gln Asp Asn Lys Leu
145                 150                 155                 160

Glu Gly Phe Phe Leu Lys Lys Asp Ile Arg Tyr Ser Phe Trp Ala Phe
                165                 170                 175

Phe Pro Ser Gly Val Leu Thr Gly Pro Lys Gly Phe Ser Leu Ser Ser
            180                 185                 190

Tyr Gly Gln Gly Ala Ser Thr Val Glu Pro Phe Leu Val Asp Glu Lys
        195                 200                 205

Lys Ile Thr Ala Lys His Ile Val Phe Val Glu Lys Arg Leu Ala
    210                 215                 220

Ala Gln Gly Ile Ile Pro Val Trp Lys Asp
225                 230

<210> SEQ ID NO 59
<211> LENGTH: 233
<212> TYPE: PRT
<213> ORGANISM: Prunus persica
<220> FEATURE:
<221> NAME/KEY: MISC_FEATURE
<222> LOCATION: (1)..(233)
<223> OTHER INFORMATION: DUF2996 domain-containing protein

<400> SEQUENCE: 59

Met Ala Ala Ile Ser Ser Val Val Gly Thr Gly Ser Val Pro Gln Ile
1               5                   10                  15

Gln Asn Arg Ser Gly Leu Ala Pro Phe Thr Pro Leu His Ile Ser Leu
            20                  25                  30

Phe Ser Pro Thr Arg Arg Leu Leu Glu Val Gly Ala Gly Arg Thr Tyr
        35                  40                  45
```

```
Thr Pro Ser Ala Ile Asp Asp Arg Thr Ser Phe Cys Leu Ser Lys Pro
        50                  55                  60

Lys Phe Asp Asn Ala Ser His Thr Val Ser Lys Leu Val Thr Ser Gln
 65                  70                  75                  80

Arg Asn Ile Val Cys Ser Ala Leu Pro Glu Ser Ser Thr Ser Thr Val
                    85                  90                  95

Ala Ala Asp Thr Lys Glu Val Lys Thr Ala Gln Lys Ala Ala Pro Ala
                100                 105                 110

Lys Pro Lys Val Ala Ala Lys Ala Pro Val Lys Pro Leu Pro Gln Met
            115                 120                 125

Met Glu Glu Asp Val Ile Pro Gln Leu Lys Ala Ile Leu Glu Thr Gln
130                 135                 140

Asp Glu Leu Ser Asp Ile Glu Leu Ser Phe Gln Glu Asn Lys Leu Glu
145                 150                 155                 160

Gly Phe Phe Leu Lys Lys Asp Ile Arg Tyr Ser Phe Trp Ala Phe Phe
                165                 170                 175

Pro Ser Gly Val Leu Thr Gly Pro Lys Gly Phe Ser Leu Ser Ser Tyr
                180                 185                 190

Gly Gln Gly Ala Ser Thr Val Glu Pro Phe Leu Ile Asp Glu Lys Lys
            195                 200                 205

Ile Thr Ala Lys His Ile Val Phe Trp Val Glu Lys Arg Leu Ala Ala
210                 215                 220

Gln Gly Ile Ile Pro Val Trp Lys Asp
225                 230

<210> SEQ ID NO 60
<211> LENGTH: 225
<212> TYPE: PRT
<213> ORGANISM: Pyrus x bretschneideri
<220> FEATURE:
<221> NAME/KEY: MISC_FEATURE
<222> LOCATION: (1)..(225)
<223> OTHER INFORMATION: DUF2996 domain-containing protein

<400> SEQUENCE: 60

Met Lys Leu Gln Ile Asn His Gln Ala Ser Met Ala Ser Ala Ile Leu
 1               5                  10                  15

Ser Leu Ala Lys Pro Ser Pro Leu Gln Val Gln Pro Asn Gly Lys His
                20                  25                  30

Phe Ala Glu Phe Ser Ala Leu Pro Lys Pro Ser Ala Ser Leu Pro Phe
            35                  40                  45

Gly Arg Lys Thr Ser Asn Asp Gln Met Met Lys Ser Lys Val Val Ala
 50                  55                  60

Ser Gln Arg Asn Ile Ala Cys Phe Ala Leu Gln Glu Ser Ser Thr Ser
 65                  70                  75                  80

Thr Gly Glu Ala Asp Ala Ala Asp Thr Ser Thr Lys Glu Val Lys Thr
                85                  90                  95

Ala Asp Gln Lys Ala Ala Ala Pro Ala Lys Pro Lys Val Ala Ala Lys
                100                 105                 110

Ala Pro Met Lys Ala Leu Pro Gln Met Met Val Glu Asp Val Ile Pro
            115                 120                 125

Pro Leu Lys Ala Ile Leu Glu Thr Gln Asp Glu Leu Ser Asp Ile Glu
130                 135                 140

Leu Cys Phe Gln Asp Asn Arg Leu Glu Gly Ser Phe Ile Lys Lys Gly
145                 150                 155                 160
```

```
Asn Phe Tyr Ser Phe Trp Ala Phe Phe Pro Ser Gly Val Leu Thr Gly
                165                 170                 175

Pro Lys Gly Phe Ser Leu Ser Ser Tyr Gly Ser Gly Val Ser Thr Val
            180                 185                 190

Glu Pro Phe Leu Ile Asp Glu Lys Lys Ile Thr Ala Lys His Ile Val
        195                 200                 205

Phe Trp Val Glu Lys Arg Leu Ala Ala Gln Gly Ile Ile Pro Val Trp
    210                 215                 220

Asn
225

<210> SEQ ID NO 61
<211> LENGTH: 197
<212> TYPE: PRT
<213> ORGANISM: Brassica napus
<220> FEATURE:
<221> NAME/KEY: MISC_FEATURE
<222> LOCATION: (1)..(197)
<223> OTHER INFORMATION: DUF2996 domain-containing protein

<400> SEQUENCE: 61

Met Thr Ala Ile Val Gly Val Ser Phe Gly Ala Thr Ser Ser His Ile
1               5                   10                  15

Ser Ile Val Thr Pro Thr Leu Ser Ser Ser Leu Phe Pro Pro Leu
            20                  25                  30

Thr Leu His Gln Ser Gly Asn Lys Glu Ser Gln Leu Arg Cys Ala
            35                  40                  45

Val Gln Glu Ser Ser Thr Ser Ala Val Ala Thr Glu Lys Lys Glu Lys
    50                  55                  60

Glu Asp Ser Thr Val Glu Val Pro Ala Lys Asn Pro Lys Pro Ala Ala
65                  70                  75                  80

Ala Lys Ala Ser Val Ala Lys Pro Leu Arg Glu Met Met Glu Glu Asp
                85                  90                  95

Val Ile Pro Pro Leu Lys Ala Ile Leu Glu Ala Gln Asp Asp Ile Ser
            100                 105                 110

Glu Ile Asp Leu Ser Phe His Asp Asp Lys Leu Glu Gly Phe Phe Phe
        115                 120                 125

Lys Lys Gly Ile Gln Tyr Ser Phe Trp Ala Phe Phe Pro Ser Gly Asn
    130                 135                 140

Leu Thr Gly Ala Lys Gly Phe Ser Ile Ser Ser Tyr Gly Ser Gly Pro
145                 150                 155                 160

Ser Thr Val Glu Pro Phe Leu Val Asp Glu Arg Asn Pro Thr Ala Asn
                165                 170                 175

His Val Val Phe Trp Val Glu Lys Arg Leu Ala Ala Gln Gly Ile Ile
            180                 185                 190

Pro Val Trp Asn Gln
            195

<210> SEQ ID NO 62
<211> LENGTH: 193
<212> TYPE: PRT
<213> ORGANISM: Ipomoea nil
<220> FEATURE:
<221> NAME/KEY: MISC_FEATURE
<222> LOCATION: (1)..(193)
<223> OTHER INFORMATION: DUF2996 domain-containing protein

<400> SEQUENCE: 62

Met Ala Ala Thr Thr Gly Gly Ser Ile Ala Ala Leu Ser Ser Phe Arg
```

-continued

```
1               5                   10                  15
Ser Ser Ser Ser Leu Ser Arg Lys Ala Lys Ser Gly Thr Cys Val Pro
                20                  25                  30

Val Ile Cys Arg Val Val Phe Pro Gln Arg Asn Ile Ala Cys Phe Ala
                35                  40                  45

Val Gln Glu Ser Ser Ala Ala Val Ala Ala Glu Thr Lys Lys Glu Glu
                50                  55                  60

Glu Pro Val Glu Thr Glu Lys Pro Arg Lys Pro Val Ala Lys
65                  70                  75                  80

Ala Pro Ala Lys Pro Leu Pro Gln Met Met Glu Glu Asp Val Ile Pro
                85                  90                  95

Ser Leu Lys Ser Thr Leu Gln Ala Gln Asp Asp Ile Thr Glu Leu Glu
                100                 105                 110

Leu Ser Phe Asn Asp Asn Lys Leu Glu Gly Ser Phe Leu Lys Lys Gly
                115                 120                 125

Tyr Pro Tyr Ser Phe Trp Ala Phe Phe Pro Asn Gly Leu Thr Gly Pro
                130                 135                 140

Lys Gly Phe Ser Leu Ser Ser Tyr Gly Asn Gly Ala Ser Thr Val Glu
145                 150                 155                 160

Pro Phe Leu Val Asp Glu Lys Lys Ile Thr Glu Lys His Ile Val Phe
                165                 170                 175

Trp Val Glu Lys Arg Leu Ala Ala Gln Gly Ile Ile Pro Val Trp Lys
                180                 185                 190

Glu
```

<210> SEQ ID NO 63
<211> LENGTH: 234
<212> TYPE: PRT
<213> ORGANISM: Prunus mume
<220> FEATURE:
<221> NAME/KEY: MISC_FEATURE
<222> LOCATION: (1)..(234)
<223> OTHER INFORMATION: DUF2996 domain-containing protein

<400> SEQUENCE: 63

```
Met Ala Ala Ile Ser Ser Val Val Gly Thr Gly Ser Val Pro Gln Ile
1               5                   10                  15

Gln Asn Arg Ser Gly Leu Ala Pro Phe Thr Pro Leu His Thr Ser Leu
                20                  25                  30

Phe Ser Pro Thr Arg Arg Leu Leu Glu Val Gly Ala Gly Arg Thr Ser
                35                  40                  45

Thr Leu Ser Ala Ile Asp Asp Arg Thr Thr Phe Cys Leu Ser Lys Pro
                50                  55                  60

Lys Phe Asp Asn Ala Gly Gln His Thr Val Ser Lys Leu Val Thr Ser
65                  70                  75                  80

Gln Arg Asn Ile Val Cys Ser Ala Leu Pro Glu Ser Ser Thr Ser Thr
                85                  90                  95

Val Ala Ala Asp Thr Lys Glu Val Lys Thr Ala Gln Lys Ala Ala Pro
                100                 105                 110

Ala Lys Pro Lys Val Ala Ala Lys Ala Pro Val Lys Pro Leu Pro Gln
                115                 120                 125

Met Met Glu Glu Asp Val Ile Pro Gln Leu Lys Ala Ile Leu Glu Thr
                130                 135                 140

Gln Asp Glu Leu Ser Asp Ile Glu Leu Ser Phe Gln Asp Asp Lys Leu
145                 150                 155                 160
```

```
Glu Gly Leu Phe Leu Lys Lys Asp Ile Arg Tyr Ser Phe Trp Ala Phe
            165                 170                 175

Phe Pro Gly Gly Val Leu Thr Gly Pro Lys Gly Phe Ser Leu Ser Ser
        180                 185                 190

Tyr Gly Gln Gly Ala Ser Thr Val Glu Pro Phe Leu Ile Asp Glu Lys
            195                 200                 205

Lys Ile Thr Ala Lys His Ile Val Phe Trp Val Glu Lys Arg Leu Ala
210                 215                 220

Ala Gln Gly Ile Ile Pro Val Trp Lys Asp
225                 230

<210> SEQ ID NO 64
<211> LENGTH: 214
<212> TYPE: PRT
<213> ORGANISM: Lupinus angustifolius
<220> FEATURE:
<221> NAME/KEY: MISC_FEATURE
<222> LOCATION: (1)..(214)
<223> OTHER INFORMATION: DUF2996 domain-containing protein

<400> SEQUENCE: 64

Met Gln Met Thr Ile Leu Leu Arg Gly Val Leu Gly Asp Ser Ser
1               5                   10                  15

Phe Ser Phe Trp Ser Leu Thr Ser Pro Ser Ser Ser Leu His Ala Ser
            20                  25                  30

His Asn Val Ile Pro Thr Ser Ser Ser Leu Val Leu Pro Leu Ile
            35                  40                  45

Val Ser Lys Phe Lys Thr Ser Asn Arg Asn Lys Ile Thr Arg Phe Ala
50                  55                  60

Val Gln Glu Ser Ser Thr Ser Thr Thr Ala Ser Ala Glu Thr Glu Thr
65                  70                  75                  80

Lys Thr Lys Glu Ile Lys Ala Ala Pro Lys Ala Glu Pro Thr Gln Lys
                85                  90                  95

Lys Pro Leu Ala Lys Ala Pro Ala Lys Ser Leu Pro Gln Met Met Glu
            100                 105                 110

Glu Asp Val Ile Pro Ser Leu Lys Ala Ile Phe Glu Ala Gln Glu Asp
        115                 120                 125

Leu Ser Asp Ile Glu Leu Val Phe Gln Asp Asn Lys Leu Glu Gly Ser
130                 135                 140

Phe Val Asn Lys Gly Tyr Pro Tyr Ser Phe Trp Ala Phe Pro Thr
145                 150                 155                 160

Gly Leu Thr Gly Pro Lys Gly Phe Ser Leu Ser Ser Tyr Asn Ser Gly
                165                 170                 175

Ser Ser Thr Ile Glu Pro Phe Leu Val Asp Glu Lys Lys Ile Thr Ala
            180                 185                 190

Arg His Ile Ile Phe Trp Val Glu Lys Arg Leu Ala Ala Gln Gly Ile
        195                 200                 205

Ile Pro Val Trp Lys Glu
    210

<210> SEQ ID NO 65
<211> LENGTH: 225
<212> TYPE: PRT
<213> ORGANISM: Herrania umbratica
<220> FEATURE:
<221> NAME/KEY: MISC_FEATURE
<222> LOCATION: (1)..(225)
<223> OTHER INFORMATION: DUF2996 domain-containing protein
```

-continued

```
<400> SEQUENCE: 65

Met Ala Thr Leu Gly Gly Arg Ala Ile Gly Phe Ser Ser Phe Pro Ser
1               5                   10                  15

Ser Ser Ser Tyr Leu Arg Gly Asn Ser Arg Ala Thr Ser Ser Ser Phe
            20                  25                  30

Ser Cys Thr Leu Ser Met Gln Met Val Ser Lys Ser Met Ile Ser Arg
        35                  40                  45

Lys Cys Val Ala Cys Ser Ala Val Gln Glu Ser Ser Pro Thr Ala
    50                  55                  60

Thr Ala Glu Thr Lys Ala Thr Thr Pro Ala Glu Ala Lys Pro Ser Pro
65                  70                  75                  80

Thr Ser Glu Thr Lys Ala Ala Val Ala Gly Gly Lys Glu Glu Val Lys
                85                  90                  95

Ala Ala Pro Lys Ala Ala Pro Ala Arg Pro Lys Pro Ala Ala Lys Ala
            100                 105                 110

Pro Ala Lys Leu Leu Pro Glu Leu Met Ala Glu Asp Val Ile Pro Ser
        115                 120                 125

Leu Lys Thr Thr Leu Glu Ala Gln Val Asp Leu Ser Glu Ile Glu Leu
    130                 135                 140

Ser Phe Gln Asp Asn Lys Leu Glu Gly Ser Phe Leu Lys Lys Gly Cys
145                 150                 155                 160

Pro Tyr Ser Phe Trp Ala Phe Phe Pro Asp Gly Val Leu Thr Gly Pro
                165                 170                 175

Lys Gly Phe Ser Leu Thr Ser Tyr Gly Ser Val Ala Ser Thr Val Glu
            180                 185                 190

Pro Phe Leu Ile Asp Glu Lys Lys Ile Thr Ala Lys His Val Val Phe
        195                 200                 205

Trp Val Glu Lys Arg Leu Ala Ala Gln Gly Ile Ile Pro Val Trp Lys
    210                 215                 220

Glu
225

<210> SEQ ID NO 66
<211> LENGTH: 185
<212> TYPE: PRT
<213> ORGANISM: Solanum lycopersicum
<220> FEATURE:
<221> NAME/KEY: MISC_FEATURE
<222> LOCATION: (1)..(185)
<223> OTHER INFORMATION: DUF2996 domain-containing protein

<400> SEQUENCE: 66

Met Ala Thr Thr Gly Gly Ser Ile Ser Leu Ser Ser Phe Pro Ser Ser
1               5                   10                  15

Ser Phe Cys Arg Lys Pro Lys Pro Ile Leu Pro Ala Asp Ser Leu Glu
            20                  25                  30

Leu Arg His Leu Lys Thr Cys Lys Asn Leu Val Cys Phe Ala Ala Gln
        35                  40                  45

Glu Ser Ser Ser Leu Thr Val Ala Glu Glu Lys Lys Glu Ser Gln Thr
    50                  55                  60

Ala Glu Glu Lys Thr Lys Ala Lys Ala Pro Asp Lys Pro Leu His Gln
65                  70                  75                  80

Met Met Glu Glu Asn Ile Ile Pro Ser Leu Lys Ala Thr Leu Glu Ser
                85                  90                  95

Gln Asn Asp Ile Leu Glu Leu Glu Leu Ser Phe Ser Glu Asn Lys Leu
            100                 105                 110
```

```
Glu Gly Ser Phe Leu Lys Lys Gly Asn Pro Tyr Ser Phe Trp Ala Phe
            115                 120                 125

Phe Pro Asp Gly Leu Thr Gly Pro Lys Gly Phe Ser Leu Ser Ser Tyr
130                 135                 140

Gly Ser Gly Ala Ser Thr Val Glu Pro Phe Leu Val Asp Glu Lys Lys
145                 150                 155                 160

Ile Thr Ala Lys His Val Val Phe Trp Val Glu Lys Arg Leu Ala Ala
                165                 170                 175

Gln Gly Ile Ile Pro Val Trp Lys Glu
            180                 185

<210> SEQ ID NO 67
<211> LENGTH: 447
<212> TYPE: PRT
<213> ORGANISM: Daucus carota
<220> FEATURE:
<221> NAME/KEY: MISC_FEATURE
<222> LOCATION: (1)..(447)
<223> OTHER INFORMATION: DUF2996 domain-containing protein

<400> SEQUENCE: 67

Met Thr Gly Gly Gly Glu Asn Glu Gly Thr Leu Glu Tyr Thr Pro Thr
1               5                   10                  15

Trp Val Ala Ala Val Cys Thr Val Ile Val Gly Ile Ser Leu Ala
            20                  25                  30

Val Glu Arg Leu Leu His Tyr Ala Gly Lys Tyr Leu Lys Lys Lys Asn
            35                  40                  45

Gln Lys Pro Leu Phe Glu Ala Leu Gln Lys Ile Lys Glu Gly Thr Ile
50                  55                  60

Val Lys Ile Cys Val Ser Arg Ser Leu Thr Glu His Leu Leu Pro Cys
65                  70                  75                  80

Pro Leu Ser Gly Lys Pro Gly Glu Glu Lys Ser Ser His Ser Lys Pro
                85                  90                  95

Glu Thr Thr Ser His Leu Arg Arg Leu Leu Glu Glu Ser Ala Asn Glu
            100                 105                 110

Gly Tyr Cys Ala Ala Lys Asp Lys Val Pro Leu Leu Pro Leu Glu Gly
            115                 120                 125

Leu His His Leu His Ile Phe Ile Phe Val Leu Ala Ile Val His Val
130                 135                 140

Thr Phe Ser Val Leu Thr Val Val Phe Gly Gly Ala Lys Ile Arg Gln
145                 150                 155                 160

Trp Lys Ala Trp Glu Asp Ala Ile Ser Gln Glu Ser Phe Asp Pro Asn
                165                 170                 175

Lys Gly Gly Val Ser Trp Ala Leu Ala Asn Ala Gln Phe Leu Arg His
            180                 185                 190

Ser Phe Phe Lys Gln Phe Tyr Gly Ser Val Thr Lys Ser Asp Tyr Val
            195                 200                 205

Ala Leu Arg Leu Gly Phe Ile Thr Leu Leu Leu Ala Val Gly Thr Lys
210                 215                 220

Leu Glu His Ile Ile Ser Gln Leu Ala His Glu Val Ala Glu Lys His
225                 230                 235                 240

Val Ala Ile Glu Gly Glu Leu Val Val His Pro Ser Asp Asp His Phe
                245                 250                 255

Trp Phe Asn Arg Pro Lys Ile Ile Leu Phe Leu Ile His Phe Ile Leu
            260                 265                 270
```

-continued

```
Phe Gln Asn Ala Phe Glu Ile Ala Phe Phe Phe Trp Ile Trp Met Val
        275                 280                 285
Asn Thr Ala Val Ala Ser His Arg Ser Ile Ala Cys Ser Ala Val Gln
    290                 295                 300
Glu Ser Ser Ala Ser Ala Ser Ala Ser Thr Val Ser Thr Ala Asp Val
305                 310                 315                 320
Lys Glu Lys Pro Lys Pro Lys Ala Lys Pro Pro Ala Lys Ala Pro Ala
                325                 330                 335
Lys Pro Leu Pro Gln Met Met Glu Glu Asp Val Ile Pro Pro Leu Lys
                340                 345                 350
Ser Ile Leu Glu Thr Gln Glu Asp Ile Ser Glu Ile Glu Leu Ser Phe
        355                 360                 365
Glu Asp Asn Arg Leu Tyr Gly Ser Phe Val Lys Lys Asn Ile Arg Tyr
    370                 375                 380
Ser Phe Trp Ala Phe Phe Pro Asp Gly Val Leu Thr Gly Pro Lys Gly
385                 390                 395                 400
Phe Ser Leu Ser Ser Tyr Gly Ser Glu Val Ser Thr Leu Glu Pro Phe
                405                 410                 415
Leu Ile Asp Glu Lys Lys Ile Thr Ala Lys His Ile Val Phe Trp Val
                420                 425                 430
Glu Lys Arg Leu Ala Ala Gln Gly Ile Ile Pro Val Trp Arg Glu
        435                 440                 445
```